(12) United States Patent
Cooks et al.

(10) Patent No.: US 11,710,626 B2
(45) Date of Patent: Jul. 25, 2023

(54) SYSTEMS AND METHODS FOR SAMPLE ANALYSIS USING SWABS

(71) Applicant: Purdue Research Foundation, West Lafayette, IN (US)

(72) Inventors: Robert Graham Cooks, West Lafayette, IN (US); Alan Keith Jarmusch, Lafayette, IN (US); Valentina Pirro, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 65 days.

(21) Appl. No.: 17/222,194

(22) Filed: Apr. 5, 2021

(65) Prior Publication Data

US 2022/0005681 A1  Jan. 6, 2022

Related U.S. Application Data

(63) Continuation of application No. 16/101,647, filed on Aug. 13, 2018, now Pat. No. 10,998,178.
(Continued)

(51) Int. Cl.
| | |
|---|---|
| *G01N 30/72* | (2006.01) |
| *H01J 49/04* | (2006.01) |
| *A61B 5/145* | (2006.01) |
| *A61B 5/00* | (2006.01) |
| *H01J 49/16* | (2006.01) |
| *A61F 13/38* | (2006.01) |

(Continued)

(52) U.S. Cl.
CPC ...... *H01J 49/0459* (2013.01); *A61B 5/14503* (2013.01); *A61B 5/7282* (2013.01); *A61B 10/02* (2013.01); *A61F 13/38* (2013.01); *G01N 30/72* (2013.01); *H01J 49/0409* (2013.01); *H01J 49/165* (2013.01); *G01N 2001/028* (2013.01)

(58) Field of Classification Search
None
See application file for complete search history.

(56) References Cited

U.S. PATENT DOCUMENTS

| 5,310,653 A | 5/1994 | Hanausek-Walaszek et al. |
| 5,643,729 A | 7/1997 | Taniguchi et al. |
| (Continued) | | |

FOREIGN PATENT DOCUMENTS

WO   2009/023361 A2   2/2009

OTHER PUBLICATIONS

Bonner, 1977, The Cylindrical Ion Trap, International Journal of Mass Spectrometry and Ion Physics, 24(3):255-269.
(Continued)

*Primary Examiner* — Xiaoyun R Xu
(74) *Attorney, Agent, or Firm* — Brown Rudnick LLP; Adam M. Schoen

(57) ABSTRACT

The invention generally relates to systems and methods for sample analysis using swabs. In certain aspects, the invention provides systems that include a probe having a conductive proximal portion coupled to a porous material at a distal portion of the probe that is configured to retain a portion of a sample that has contacted the porous material, and a mass spectrometer having an inlet. The system is configured such that the porous material at a distal portion of the probe is aligned over the inlet of the mass spectrometer.

11 Claims, 15 Drawing Sheets

Related U.S. Application Data

(60) Provisional application No. 62/550,927, filed on Aug. 28, 2017.

(51) Int. Cl.
*A61B 10/02* (2006.01)
*G01N 1/02* (2006.01)

(56) References Cited

U.S. PATENT DOCUMENTS

| | | |
|---|---|---|
| 5,644,131 A | 7/1997 | Hansen |
| 5,840,506 A | 11/1998 | Giordano |
| 5,858,655 A | 1/1999 | Arnold |
| 5,888,746 A | 3/1999 | Tabiti et al. |
| 5,989,815 A | 11/1999 | Skolnick et al. |
| 6,008,003 A | 12/1999 | Haak-Frendscho et al. |
| 6,130,052 A | 10/2000 | Van Baren et al. |
| 6,171,796 B1 | 1/2001 | An et al. |
| 6,268,165 B1 | 7/2001 | O'Brien |
| 6,294,344 B1 | 9/2001 | O'Brien |
| 6,316,208 B1 | 11/2001 | Roberts et al. |
| 6,316,213 B1 | 11/2001 | O'Brien |
| 6,576,420 B1 | 6/2003 | Carson et al. |
| 6,682,890 B2 | 1/2004 | Mack et al. |
| 6,767,704 B2 | 7/2004 | Waldman et al. |
| 6,838,666 B2 | 1/2005 | Ouyang et al. |
| 6,841,350 B2 | 1/2005 | Ogden et al. |
| 6,897,018 B1 | 5/2005 | Yuan et al. |
| 6,905,844 B2 | 6/2005 | Kim |
| 6,936,417 B2 | 8/2005 | Orntoft |
| 6,942,978 B1 | 9/2005 | O'Brien |
| 6,974,667 B2 | 12/2005 | Horne et al. |
| 6,979,342 B2 | 12/2005 | Lee et al. |
| 6,998,232 B1 | 2/2006 | Feinstein et al. |
| 7,022,472 B2 | 4/2006 | Robbins et al. |
| 7,049,072 B2 | 5/2006 | Seshi |
| 7,056,674 B2 | 6/2006 | Baker et al. |
| 7,078,180 B2 | 7/2006 | Genetta |
| 7,081,340 B2 | 7/2006 | Baker et al. |
| 7,090,983 B1 | 8/2006 | Muramatsu et al. |
| 7,153,700 B1 | 12/2006 | Pardee et al. |
| 7,163,801 B2 | 1/2007 | Reed |
| 7,171,311 B2 | 1/2007 | Dai et al. |
| 7,198,899 B2 | 4/2007 | Schleyer et al. |
| 7,229,770 B1 | 6/2007 | Price et al. |
| 7,291,462 B2 | 11/2007 | O'Brien et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,416,851 B2 | 8/2008 | Davi et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,524,633 B2 | 4/2009 | Sidransky |
| 7,527,933 B2 | 5/2009 | Sahin et al. |
| 8,304,718 B2 | 11/2012 | Ouyang et al. |
| 8,704,167 B2 | 4/2014 | Cooks et al. |
| 8,859,956 B2 | 10/2014 | Ouyang et al. |
| 2003/0224509 A1 | 12/2003 | Moon et al. |
| 2003/0232356 A1 | 12/2003 | Dooley et al. |
| 2004/0018525 A1 | 1/2004 | Wirtz et al. |
| 2004/0053247 A1 | 3/2004 | Cordon-Cardo et al. |
| 2004/0146921 A1 | 7/2004 | Eveleigh et al. |
| 2005/0048467 A1 | 3/2005 | Sastry et al. |
| 2005/0095611 A1 | 5/2005 | Chan et al. |
| 2005/0100895 A1 | 5/2005 | Waldman et al. |
| 2005/0152908 A1 | 7/2005 | Liew et al. |
| 2005/0260566 A1 | 11/2005 | Fischer et al. |
| 2006/0046257 A1 | 3/2006 | Pollock et al. |
| 2006/0110759 A1 | 5/2006 | Paris et al. |
| 2006/0115821 A1 | 6/2006 | Einstein et al. |
| 2006/0160762 A1 | 7/2006 | Zetter et al. |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0252057 A1 | 11/2006 | Raponi et al. |
| 2006/0258841 A1 | 11/2006 | Michl et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2007/0053896 A1 | 3/2007 | Ahmed et al. |
| 2007/0154889 A1 | 7/2007 | Wang |
| 2007/0184439 A1 | 8/2007 | Guilford et al. |
| 2007/0259368 A1 | 11/2007 | An et al. |
| 2007/0292869 A1 | 12/2007 | Becker et al. |
| 2008/0009005 A1 | 1/2008 | Kruk |
| 2008/0014590 A1 | 1/2008 | Dahary et al. |
| 2008/0020940 A1 | 1/2008 | Stedronsky et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0057514 A1 | 3/2008 | Goldenring |
| 2008/0058432 A1 | 3/2008 | Wang et al. |
| 2008/0064047 A1 | 3/2008 | Zetter et al. |
| 2008/0081333 A1 | 4/2008 | Mori et al. |
| 2008/0113340 A1 | 5/2008 | Schlegel |
| 2008/0118462 A1 | 5/2008 | Alani et al. |
| 2008/0138806 A1 | 6/2008 | Chow et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0268473 A1 | 10/2008 | Moses et al. |
| 2008/0269157 A1 | 10/2008 | Srivastava et al. |
| 2008/0274908 A1 | 11/2008 | Chang |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0017463 A1 | 1/2009 | Bhowmick |
| 2009/0023137 A1 | 1/2009 | Van Der Zee et al. |
| 2009/0029372 A1 | 1/2009 | Wewer |
| 2009/0062144 A1 | 3/2009 | Guo |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |

(56) References Cited

U.S. PATENT DOCUMENTS

| | | | |
|---|---|---|---|
| 2009/0124569 | A1 | 5/2009 | Bergan et al. |
| 2009/0127454 | A1 | 5/2009 | Ritchie et al. |
| 2009/0131353 | A1 | 5/2009 | Insel et al. |
| 2014/0224981 | A1 | 8/2014 | Owen et al. |
| 2014/0264004 | A1* | 9/2014 | Cooks .................. H01J 49/04 250/288 |

OTHER PUBLICATIONS

Cooks, 2006, Ambient Mass Spectrometry, Science 311:1566-1570.

Dill, 2010, Multivariate statistical differentiation of renal cell carcinomas based on lipidomic analysis by ambient ionization imaging mass spectrometry, Analytical and Bioanalytical Chemistry 398:2969-2978.

Dill, 2011, Multivariate Statistical Identification of Human Bladder Carcinomas Using Ambient Ionization Imaging Mass Spectrometry, A European Journal 17:2897-2902.

Dill, 2010, Multivariate statistical differentiation of renal cell carcinomas based on lipidomic analysis by ambient ionization imaging mass spectrometry, Analytical and Bioanalytical Chemistry 398, 2969-2978, published in Germany.

Eberlin, 2010, Cholesterol Sulfate Imaging in Human Prostate Cancer Tissue by Desorption Electrospray Ionization Mass Spectrometry, Analytical Chemistry 82:3430-3434.

Eberlin, 2010, Discrimination of human astrocytoma subtypes by lipid analysis using desorption electrospray ionization imaging mass spectrometry, Angew Chem Int Ed Engl 49:5953-5956.

Eberlin, 2012, Classifying human brain tumors by lipid imaging with mass spectrometry, Cancer Res 72:645-654.

Faca, 2008, A Mouse to Human Search for Plasma Proteome Changes Associated with Pancreatic Tumor Development, PLoS Med; 5(6):e123.

Fenn, 1989, Electrospray Ionization for Mass Spectrometry of Large Biomolecules, Science 246:64-71.

Fico, 2007, Miniaturization and Geometry Optimization of a Polymer-Based Rectilinear Ion Trap, Anal. Chem., 79:8076-8082.

Filella, 1994, Tag-72, CA 19.9 and CEA as Tumor Markers in Gastric Cancer, Acta Oncol. 33(7):747-751.

Gao, 2006, Handheld Rectilinear Ion Trap Mass Spectrometer, Z. Anal. Chem. 78:5994-6002.

Gao, 2008, Design and Characterization of a Multisource Hand-Held Tandem Mass Spectrometer, Z. Anal. Chem, 80:7198-7205.

Hagar, 2002, A new linear ion trap mass spectromer, Rapid Communi. Mass Spectrometry, 16(6):512-526.

Hasina, 2003, Plasminogen Activator Inhibitor-2: A Molecular Biomarker for Head and Neck Cancer Progression, Cancer Research, 63:555-559.

Hellman, 2009, Differential tissue-specific protein markers of vaginal carcinoma, Br J Cancer, 100(8):1303-1314.

Hendricks, 2014, Autonomous in-situ analysis and real-time chemical detection using a backpack miniature mass spectrometer: concept, instrumentation development and performance, Anal. Chem., 86:2900-2908.

Hou, 2011, Sampling Wand for an Ion Trap Mass Spectrometer, Anal. Chem., 83:1857-1861.

Jarmusch, 2016, Lipid and metabolite profiles of human brain tumors by desorption electrospray ionization-MS, PNAS, 113(6):1486-91.

Li, 2014, Miniature Ambient Mass Analysis System, Anal. Chem., 86:2909-2916.

Lipkin, 1988, Biomarkers of Increased susceptibility to Gastrointestinal Cancer: New Application to Studies of Cancer Prevention in Human Subjects, Cancer Research, 48:235-245.

Mulligan, 2006, Desorption electrospray ionization with a portable mass spectrometer: in situ analysis of ambient surfaces, Chem Comm, et al., Chemical Communications, 1709-1711.

Ouyang, 2009, Handheld Miniature Ion trap Mass Spectrometers, Anal Chem, 81(7):2421-2425.

Ouyang, 2009, Miniature Mass Spectrometers, Ann Rev Anal Chem, 2:187-214.

Pirro, 2017, Analysis of human gliomas by swab touch spray-mass spectrometry: applications to intraoperative assessment of surgical margins and presence of oncometabolies, Analyst, 142:449-54.

Pirro, 2017, Intraoperative assessment of tumor margins during glioma resection by desorption electrospray ionization-mass spectrometry, PNAS, 114(26):6700-6705.

Ralhan, 2008, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics, 7(6):1162-1173.

Sanders, 2009, Hand-held mass spectrometer for environmentally relevant analytes using a variety of sampling and ionization methods, Euro J Mass Spectrom, 16:11-20.

Santagata, 2014, Intraoperative mass spectrometry mapping of an onco-metabolite to guide brain tumor surgery, PNAS., 111(30):11121-6.

Sokol, 2011, Miniature mass spectrometer equipped with electrospray and desorption electrospray inonization for direct analysis of organics from solids and solutions, Int. J. Mass Spectrom., 306:187-195.

Tchagang, 2008, Early detection of ovarian cancer using group biomarkers, Mol Cancer Ther, 7(1):27-37.

Van Bockstaele, 2009, Prognostic markers in chronic lymphocytic leukemia: A comprehensive review, Blood Rev., 23:25-47.

Xu, 2010, Miniartureization of Mass Spectrometry Analysis Systems, JALA, 15(6):433-439.

Xu, 2011, Oncometabolite 2-Hydroxyglutarate is a Competitive Inhibitor of alpha- Ketoglutarate-Dependent Dioxygenases, Cancer Cell, 19:17-30.

Yamashita, 1984, Electrospray Ion Source. Another Variation on the Free-Jet Theme, J. Phys. Chem., 88:4451-4459.

\* cited by examiner

SYSTEMS AND METHODS FOR SAMPLE ANALYSIS USING SWABS

RELATED APPLICATION

The present application is a continuation of U.S. nonprovisional application Ser. No. 16/101,647, filed Aug. 13, 2018, which claims the benefit of and priority to U.S. provisional patent application Ser. No. 62/550,927, filed Aug. 28, 2017, the content of which is incorporated by reference herein in its entirety.

GOVERNMENT SUPPORT

This invention was made with government support under R21EB015722 awarded by the National Institute of Health (NIH). The government has certain rights in the invention.

FIELD OF THE INVENTION

The invention generally relates to systems and methods for sample analysis using swabs.

BACKGROUND

Biological systems are increasingly viewed and analyzed as highly complex networks of interlinked macromolecules and metabolites. Metabolites are low molecular weight compounds (<1 kDa) involved in chemical reactions that occur inside cells of living organisms to uphold life, i.e. the process of metabolism. The chemical diversity of the metabolome, defined as the complement of all detectable metabolites, is large and includes a wide range of compound classes, e.g. carbohydrates, amino acids, organic acids, and sterols. The quantity and number of metabolites vary with changing conditions such as environment, diet and in response to disease. Significant time and money has been invested in order to investigate the relationship between metabolite alterations and biochemical mechanisms, including disease processes.

Methods for analysis of the metabolome include nuclear magnetic resonance (NMR) spectroscopy, gas chromatography (GC) and liquid chromatography (LC) coupled to mass spectrometry (MS). In addition, Fourier transform InfraRed spectroscopy (FTIR) has been used together with direct infusion mass spectrometry to analyze metabolites.

NMR and FTIR require minimal sample preparation, however, detection limits are higher compared to the MS-based techniques and elucidation of spectra composed of many metabolites can be problematic. A problem with MS-based methods is that they require complex sample preparation protocols that involve sample extraction, purification, and other work-up steps prior to sample analysis. Those preparation protocols in addition to the solvents used as part of the MS analysis destroy the native morphology of the sample, making it impossible to correlate diagnostic results with their originating source.

SUMMARY

The invention presents a new technique (swab spray MS) for analysis of neurological tissue and provides data of its diagnostic utility. Swab spray MS is an ambient ionization method in which a minute amount of sample (e.g. tissue) is transferred to a swab tip by a gentle touch, and subsequently ionized with the application of solvent to the swab tip and of high voltage to the swab shaft. Analysis is straightforward and requires no other sample handling or pretreatment, making it highly appropriate for point-of-care testing. Swabs are used as both sampling devices and electrospray probes for MS analysis. This technique has use as a manual tool that allows minimally-invasive tissue sampling, performed remotely from the mass spectrometer, so that its intraoperative use does not interfere with current surgical procedures. The development of swab spray MS utilizes swabs as probes that can be utilized for in vivo sampling of deep surgical wounds, body orifices and surfaces, facilitating the translation of this tool into surgical applications. Electrospray ionization occurs readily from the porous material of the swab tip.

In certain aspects, the invention provides systems that include a probe having a conductive proximal portion coupled to a porous material at a distal portion of the probe that is configured to retain a portion of a sample that has contacted the porous material, and a mass spectrometer (bench-top or miniature having an inlet. The system is configured such that the porous material at a distal portion of the probe is aligned over the inlet of the mass spectrometer. Multiple different alignment positions are possible and a preferable alignment is such that the probe is aligned vertically over (on top of) the inlet of the mass spectrometer. Numerous tip shapes are within the scope of the invention and an exemplary tip shape for the porous material is in a fused shape.

In certain embodiments, the system also includes a voltage source operably coupled to the conductive proximal portion of the probe. In other embodiments or additional embodiments, a solvent source is also a component of the system and it is configured to apply solvent to the porous material. The solvent may include an internal standard. In other embodiments, the medical swab is attached to an electrospray ionization probe or forms a distal tip of an electrospray ionization probe. Electrospray ionization probes are described for example in Fenn et al. (Science, 246:64-71, 1989); and Yamashita et al. (J. Phys. Chem., 88:4451-4459, 1984), the content of each of which is incorporated by reference herein in its entirety.

Any mass spectrometer known in the art may be used with systems of the invention. In certain embodiments, the mass spectrometer is a miniature mass spectrometer, such as described for example in Gao et al. (Z. Anal. 15 Chem. 2006, 78, 5994-6002), Gao et al. (Anal. Chem., 80:7198-7205, 2008), Hou et al. (Anal. Chem., 83:1857-1861, 2011), Sokol et al. (Int. J. Mass Spectrom., 2011, 306, 187-195), Xu et al. (JALA, 2010, 15, 433-439); Ouyang et al. (Anal. Chem., 2009, 81, 2421-2425); Ouyang et al. (Ann. Rev. Anal. Chem., 2009, 2, 187-25 214); Sanders et al. (Euro. J. Mass Spectrom., 2009, 16, 11-20); Gao et al. (Anal. Chem., 2006, 78(17), 5994-6002); Mulligan et al. (Chem. Com., 2006, 1709-1711); and Fico et al. (Anal. Chem., 2007, 79, 8076-8082)., the content of each of which is incorporated herein by reference in its entirety.

Other aspects of the invention provide methods for analyzing a sample that involve contacting a distal portion of a probe to a sample such that a portion of the sample is retained on the distal portion of the probe. The methods may additionally involve positioning the distal portion of the probe over (on top of, e.g., vertically over) an inlet of a mass spectrometer; and applying solvent and voltage to the probe to generate ions of the sample that are downwardly expelled from the probe and into the inlet of the mass spectrometer. The methods may then involve analyzing the ions in the mass spectrometer, thereby analyzing the sample.

Any sample type may be analyzed using systems and methods of the invention. In an exemplary embodiment, the sample is an in vivo human tissue sample and a portion of the in vivo human tissue sample is retained on the distal portion of the probe. The in vivo tissue sample may originate from any location. In certain embodiments, the in vivo human tissue sample is along a surface of a resection cavity of the human. In such embodiments, the methods may further involve determining if the in vivo human tissue sample includes abnormal tissue. The abnormal tissue may be diseased tissue, such as cancerous tissue, such as cancerous tissue from a tumor.

Other aspects of the invention provide methods for assessing a tissue that involve contacting a medical swab to a tissue in a manner that a portion of the tissue is retained on the medical swab, generating ions of one or more analytes from the portion of the tissue retained on the medical swab, and analyzing the ions in a mass spectrometer, thereby assessing the tissue. In certain embodiments, the tissue is in vivo tissue. In other embodiments, the in vivo tissue is tissue at a resection site in a patient. In such embodiments, the analyzing may allow for assessment of tumor infiltration into the resection site.

BRIEF DESCRIPTION OF THE DRAWINGS

FIG. 1A shows that tissue is touched with the swab tip and transferred by rotating the swab on its shaft. The swab is positioned in front of a mass spectrometer and an electrospray is generated directly from the swab tip upon application of solvent and high voltage, which allows mass spectra to be acquired, as shown in FIG. 1B.

(FIG. 2 panel A) Sample #24; pathological assignment: grey matter with low TCP. (FIG. 2 panel B) Sample #2; pathological assignment: white matter with low TCP. (FIG. 2 panel C) Sample #20; pathological assignment: glioma with high TCP m/z.

FIG. 4 panels A, D, and G show negative ion mode full-scan mass spectra over m/z 760-920 of (FIG. 4 panel A) Sample 31, pathological assignment: glioma 70% TCP. (FIG. 4 panel D) Sample #32, pathological assignment: glioma 70% TCP (FIG. 4 panel G) Sample #33, pathological assignment, grey matter with 40% TCP. FIG. 4 panels B, E, and H show lipid profile spectra that are normalized to the base peak. Negative ion mode production scan for NAA of (FIG. 4 panel B) Sample #31, (FIG. 4 panel E) Sample #32, (FIG. 4 panel H) Sample #33. MS/MS production spectra are normalized to the signal of the internal standard NAA-d3 (transition m/z 177→116). FIG. 4 panels C, F, and I are pictures of specimen #19 with superimposed annotation of the touch number for swab spray MS analysis (FIG. 4 panel C) Touch #1. (FIG. 4 panel F) Touch #2. (FIG. 4 panel I) Touch #3. The tissue was allowed to thaw at room temperature before performing the swab spray MS analysis.

FIG. 5 panel B shows 2HG concentration (ng/mg tissue) from tissue extracts by E51-MS versus 2HG normalized signal from swab spray MS for 28 cases (case #29 was of insufficient quantity to perform the quantitative measurement). Red objects, wild-type gliomas; blue objects, IDH-mutant gliomas; black lines represent the cut-offs for the logarithmic 2HG normalized signal intensity (1.02) and for the Logarithmic 2HG concentration (45 ng/mg). The value of 0.001 was assigned to samples in which no 2HG signal was detected in order to compute the logarithm (*3).

FIG. 6 panel B is an image of electrospray generated from the swab, red laser pointer was used to illuminate the spray plume.

(FIG. 8 panel A) Total ion count (TIC) over a 10-minute window of data acquisition. Vertical red lines are drawn at minutes 1 and 9, respectively; the red arrows point at the full-scan mass spectrum acquired at those two time points. (FIG. 8 panel B) Full-scan mass spectrum in negative ion mode after 1 minutes of data acquisition; TIC=1.67.105 (FIG. 8 panelC) Full-scan mass spectrum in negative ion mode after 9 minutes of data acquisition; TIC=0.26.105.

(FIG. 10 panel B) detected in the negative ionization mode from sample #8. Characteristic losses used in determining the lipid class, e.g. −87 (m/z 788→701, head group loss of phosphatidylserines). Further, acyl chain could be determined based on fatty acid product ions, e.g. m/z 283, stearic acid.

DETAILED DESCRIPTION

Figure 1A:
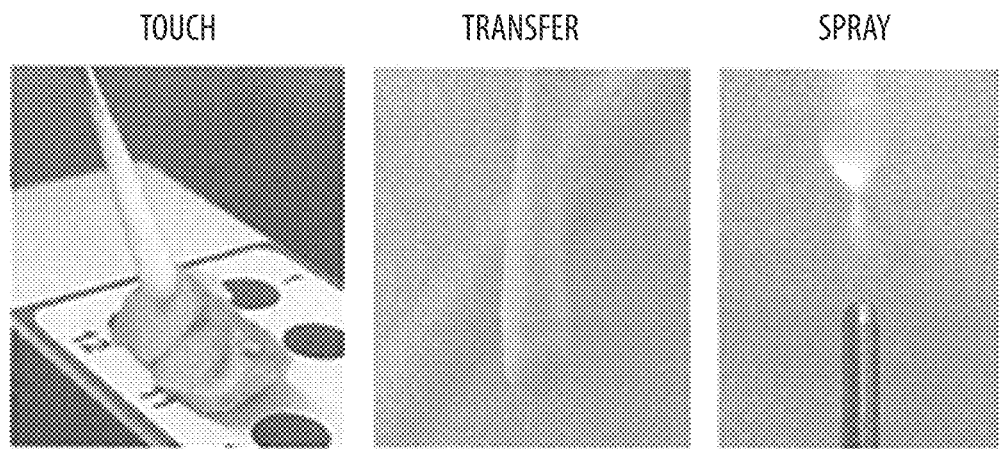
FIGS. 1A-B show the swab spray MS experiment.

The invention generally provides for the rapid analysis of tissue (e.g., neurological tissue) by swab spray MS, a technique that utilizes medical swabs. Swab spray MS is envisioned as a tool for molecular diagnosis, such as analysis of gliomas, in which tissue is sampled in vivo along the surface of a resection cavity, and then analyzed intraoperatively to provide rapid feedback on the pathological state of the tissue and so guide surgical maneuvers for maximal tumor excision. The utility of chemical pathology for surgical margin assessment is based on the added diagnostic information provided to complement standard intraoperative histopathology. Intraoperative histopathology identifies tumor type and grade from tumor core tissue, but it is not used for assessment of surgical margins since sample preparation is time-demanding and readings are unreliable from suboptimal preparations. Surgical margins are defined based on the surgeon's experience, visual and tactile observation of the tissue during surgery, and neuronavigation according to preoperative MRI. No intrasurgical molecular measurement indicative of tissue pathology is currently made to assist in surgical decision-making.

Three items of information were sought from the mass spectra obtained using swab spray MS: (I) tissue type by monitoring the expression of complex phospholipids; (ii) tumor infiltration measured as percentage of tumor cells (TCP) by monitoring the abundance of N-acetylaspartate (NAA); and (iii) assessment of the isocitrate dehydrogenase (IDH) mutation status by monitoring the presence of the oncometabolite 2-hydroxyglutarate (2HG). Previous studies using desorption electrospray ionization-mass spectrometry (DESI-MS) prove that all three items of diagnostic information are achievable by electrospray-based ambient ionization MS (Cooks et al., Science 2006; 311:1566-70; Jarmusch et al., Proc Natl Acad Sci USA 2016; 113:1486-91; Pirro et al., Analyst 2017; 142:449-54; and Santagata et al., Proc Natl Acad Sci USA 2014; 111:11121-6, the content of each of which is incorporated by reference herein in its entirety) and that such a technology can be used for intraoperative molecular pathology. DESI-MS is emerging as molecular diagnostic intraoperative tool for analysis ex vivo of biopsied tissue smears. Phospholipid profiles, as detected by DESI-MS change dynamically with the density of the tumor and with the composition of the infiltrated brain parenchyma (i.e. grey matter, white matter, or a mixture of both). NAA abundance in DESI mass spectra decreases proportionally with the degree of tumor infiltration (measured as TCP) into the tissue. 2HG accumulates in glioma tissue carrying IDH mutations. Its presence has been determined using DESI-MS and the data compared well with clinical genetic tests. The development of swab spray MS represents an additional step towards the implementation of intraoperative MS by providing the a surgeon with a simple tool for in vivo tissue sampling and direct MS analysis for chemical evaluation of tissue pathology.

The skilled artisan will appreciate that while the above, and certain aspects herein, refer to biomarkers in neurological tissue and certain neurological cancers, the approach outlined above is applicable to any tissues and any diseases having known biomarkers. For example, the approach outlined above can be used to analyze any surgical site for which tissue resection is occurring. The sample can be analyzed from the swab to look for the known biomarker that is correlated with the patient's particular cancer. The result provided to the surgeon inform the surgeon as to whether additional tissue need to be resected. Additionally, other diseases besides cancer have known associated biomarkers, and thereof other diseases are within the scope of the invention.

Further, the invention is applicable outside of the field of tissue resection. For example, the systems and methods of the invention are applicable to wound care and wound analysis. Wounds may be swabbed and analyzed for, for example, presence of microorganisms. Microorganism identification and analysis is described for example in U.S. Pat. No. 8,704,167, the content of which is incorporated by reference herein in its entirety. Other biomarkers from wounds can also be analyzed. The invention also extends to analysis of any type of skin condition, e.g., rashes or other conditions of the skin, for which analysis may be desired.

Figure 6A:
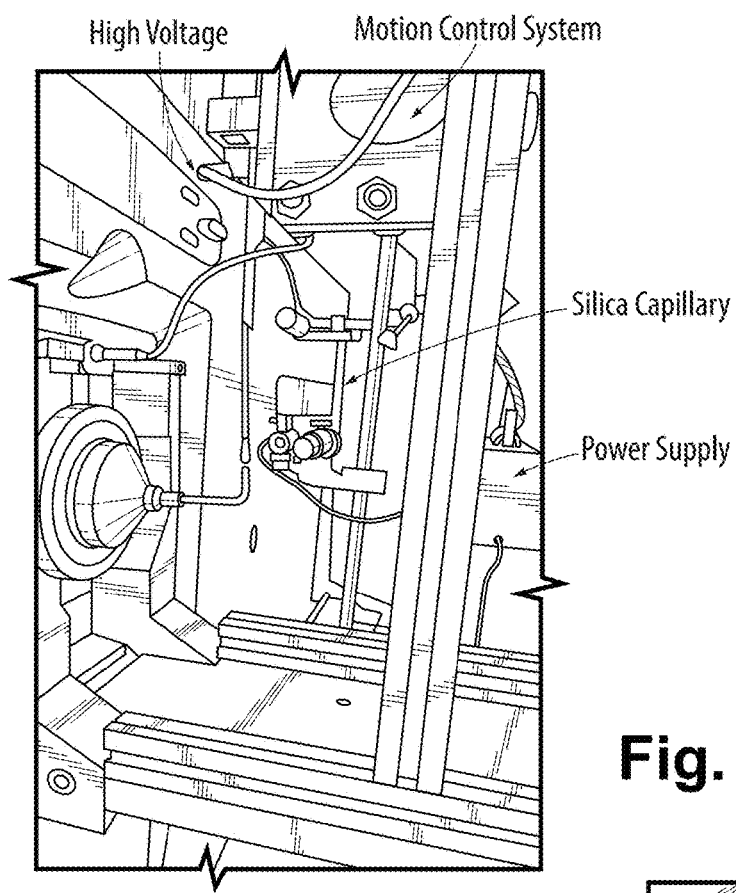
FIG. 6 panel A is an image of the custom-build ion source for swab spray MS with medical swabs.
Figure 6B:
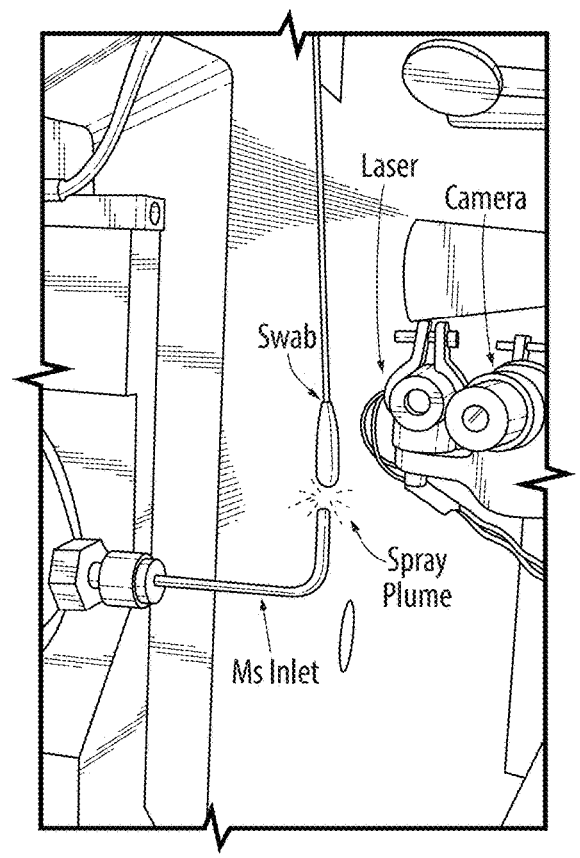
Figure 12:
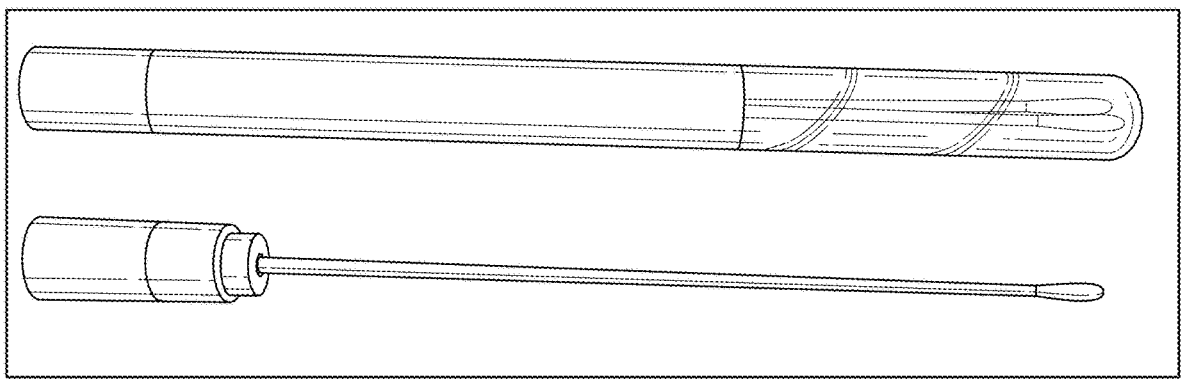
FIG. 12 is a photograph of medical swabs, model 160 C, from Copan Diagnostics with and without the plastic sealing tube.

Referring now to a particular embodiment related to analysis of neurological tissues, cryopreserved human neurological specimens were obtained from 29 patients through the Biorepository of the Methodist Research Institute (Purdue IRB #1410015344). Tissue specimens were stored at −80° C. before analysis. The tissue was cryo-sectioned to expose a flat surface, then the tissue was allowed to thaw at room temperature. A region of interest of the tissue (approximately 6 mm$^2$) was touched using the swab and MS analysis was executed directly from the swab tip as shown in FIG. 1A and FIG. 6 panels A-B. Swabs were purchased from Copan Diagnostics and have a sterile mini tip made of rayon and an aluminum handle (FIG. 12). Minute quantities of tissue were transferred onto the swab tip by rotating the swab on its shaft, and then analyzed directly using MS (FIG. 1A). For samples showing macroscopically-heterogeneous areas, multiple regions of interest were touched and analyzed independently (Table 1).

TABLE 1

Table S1.
Pathological Evaluation and Chemical Assessments

|      |         | Tissue         |                |           | Pathological Evaluation   |      |         | Chemical Assessment         |      |                          |                          |
|------|---------|----------------|----------------|-----------|---------------------------|------|---------|-----------------------------|------|--------------------------|--------------------------|
|      |         | Weight         | # Samples in   |           |                           |      |         | Base Peak<br>Lipid Profile  |      | NAA<br>(Norm.            | 2HG<br>(Norm.            |
| Case | Touches | (mg)           | Main Text      | Diagnosis | Comments$^a$              | TCP  | IDH$^b$ | (m/z)                       | S/N  | Signal)                  | Signal)                  |
| 1    | 1       | 1.9            | 1              | IT        | Mostly WM                 | Low  | 0       | 888.6                       | 58   | 623                      | 0.18                     |
|      | 2       | 3.1            | 2              | IT        | Mixture of GM and WM      | Low  |         | 834.4                       | 63   | 344                      |                          |
| 2    | 1       | 4.5            | 3              | G         | Presence of necrosis      | High | 0       | n.d.$^c$                    | n.d. | 2.4                      | n.d.                     |
| 3    | 1       | 4.9            | 4              | G         | —                         | High | 1       | 788.4                       | 27   | 8.2                      | 1.34                     |
|      | 2       | n/a            | 5              | G         | —                         | High |         | 794.4                       | 17   | 6.9                      |                          |

TABLE 1-continued

Table S1.
Pathological Evaluation and Chemical Assessments

| Case | # Touches | Tissue Weight (mg) | # Samples in Main Text | Pathological Evaluation Diagnosis | Comments[a] | TCP | IDH[b] | Base Peak Lipid Profile (m/z) | S/N | NAA (Norm. Signal) | 2HG (Norm. Signal) |
|---|---|---|---|---|---|---|---|---|---|---|---|
| 4 | 1 | 3.5 | 6 | G | Mostly necrotic and hemorrhagic tissue. | High | 0 | 885.5 | 36 | 3.1 | n.d. |
| 5 | 1 | 5.4 | 7 | IT | Infiltrated GM | Medium | 1 | 834.4 | 62 | 52.5 | 10.51 |
| 6 | 1 | 1.9 | 8 | IT | Mixture of GM and WM | Low | 0 | 888.6 | 71 | 236 | 0.14 |
|   | 2 | 1.5 | 9 | IT | GM | Low |   | 834.5 | 45 | 179 |   |
| 7 | 1 | 1.2 | 10 | G | Presence of calcification | High | 1 | 885.5 | 18 | 10.1 | 18.22 |
|   | 2 | 1.1 | 11 | G | Presence of calcification | High |   | 885.5 | 42 | 19.0 |   |
| 8 | 1 | 1.8 | 12 | IT | Mostly GM | Low | 0 | 834.4 | 50 | 531 | 0.19 |
|   | 2 | 1.8 | 13 | IT | Mostly WM | Low |   | 888.6 | 226 | 232 |   |
| 9 | 1 | 3.3 | 14 | G | — | High | 0 | 885.5 | 45 | 7.8 | 0.09 |
|   | 2 | 3.7 | 15 | G | — | High |   | 885.5 | 52 | 1.6 |   |
| 10 | 1 | 3.2 | 16 | IT | Mixture of GM (90%) and WM (10%) | Low | 0 | 834.5 | 36 | 131 | 0.63 |
|   | 2 | 1.0 | 17 | IT (nos) | — | Low |   | 888.5 | 130 | 1063 |   |
| 11 | 1 | 1.7 | 18 | IT | Mostly WM | Low | 0 | 888.6 | 88 | 81.0 | 0.40 |
|   | 2 | 1.9 | 19 | IT (nos) | — | Low |   | 888.6 | 157 | 171 |   |
| 12 | 1 | 2.5 | 20 | G | — | High | 0 | 794.4 | 10 | 1.9 | 0.08 |
| 13 | 1 | 1.6 | 21 | G | Mostly necrotic tissue | High | 0 | 885.5 | 11 | n.d. | n.d. |
| 14 | 1 | 1.8 | 22 | IT | Mixture of WM (50%) and GM (50%) | Low | 0 | 834.4 | 83 | 150 | 0.17 |
|   | 2 | 2.5 | 23 | IT | Mixture WM (50%) and GM (50%) | Low |   | 888.6 | 38 | 89.2 |   |
| 15 | 1 | 1.8 | 24 | IT | Mostly GM | Low | 1 | 834.4 | 22 | 99.6 | 1.63 |
| 16 | 1 | 8.6 | 25 | IT (nos) | — | Medium | 1 | 794.4 | 31 | 10.1 | 25.33 |
|   | 2 | 4.7 | 26 | IT (nos) | — | Medium |   | 794.4 | 28 | 63.0 |   |
| 17 | 1 | 3.1 | 27 | IT | Mostly WM | Low | 0 | 888.6 | 57 | 23.6 | 0.14 |
|   | 2 | 2.6 | 28 | IT | Mostly GM | Low |   | 834.4 | 58 | 249 |   |
| 18 | 1 | 3.9 | 29 | IT | Mostly GM | Medium | 0 | 834.4 | 113 | 71.8 | 0.63 |
|   | 2 | 4.3 | 30 | IT | Mixture of GM and WM | Medium |   | 794.4 | 28 | 88.4 |   |
| 19 | 1 | 2.4 | 31 | G | — | High | 1 | 794.5 | 29 | 22.3 | 6.54 |
|   | 2 | 2.7 | 32 | G | — | high |   | 788.4 | 15 | 7.91 |   |
|   | 3 | 3.5 | 33 | G | Infiltrated GM | Medium |   | 834.5 | 84 | 29.6 |   |
| 20 | 1 | 2.4 | 34 | IT | Mostly GM | Low | 0 | 834.5 | 30 | 117 | n.d. |
| 21 | 1 | 3.5 | 35 | IT | Mostly GM | Low | 1 | 794.4 | 28 | 101 | 23.51 |
|   | 2 | 2.2 | 36 | IT | Mixture of GM (65%) and WM (35%) | Low |   | 788.4 | 3 | 165 |   |
| 22 | 1 | 4.0 | 37 | IT | Mostly GM with small pockets of WM | Low | 0 | 834.5 | 58 | 277 | 0.17 |
|   | 2 | 4.1 | 38 | IT | Mostly GM | Low |   | 834.5 | 136 | 227 |   |
| 23 | 1 | 4.7 | 39 | IT | GM | Low | 0 | 834.5 | 24 | 419 | 0.78 |
| 24 | 1 | 2.4 | 40 | IT | Mostly GM | Low | 0 | 834.4 | 45 | 312 | 0.04 |
|   | 2 | 1.3 | 41 | IT | Mostly GM | Low |   | 834.4 | 113 | 207 |   |
| 25 | 1 | 8.6 | 42 | IT (nos) | Presence of edema | Medium | 0 | 788.4 | 43 | 1.67 | 0.04 |
| 26 | 1 | 2.4 | 43 | IT | Mixture of GM and WM | Medium | 0 | 888.6 | 55 | 31.7 | 0.22 |
| 27 | 1 | 1.3 | 44 | IT | Mostly GM | Low | 0 | 834.5 | 77 | 441 | 0.52 |
| 28 | 1 | 1.0 | 45 | IT | Mostly GM | Low | 0 | 834.5 | 42 | 383 | 0.02 |
|   | 2 | 1.1 | 46 | IT | Mixture of GM and WM | Low |   | 888.6 | 91 | 191 |   |
| 29 | 1 | 3.5 | 47 | G | — | High | 1 | 835.5 | 74 | 3.5 | 3.62 |

[a] GM, grey matter; WM, white matter; G, glioma; IT, infiltrated tissue; IT (nos), Infiltrated tissue not otherwise specified
[b] 0 = non-immunoreactive; 1 = immunoreactive
[c] n.d. = not detected MS experiments were performed using the set-up shown in FIG. 6 panels A-B. A linear ion trap mass spectrometer (Finnigan LTQ, Thermo Electron Corporation) was used. The ion source was custom-built to allow positioning the swab vertically with respect to the mass spectrometer. The use of an extended MS inlet capillary, bent 90 ° upwards and held directly underneath the swab tip, improved stability of the swab electrospray (FIG. 6 panels A-B). The MS inlet, can be bent at other angles and the invention is not limited to a 90 degree bend of the MS inlet.

The skilled artisan will appreciate that vertically, e.g., directly aligned above, is a most preferred embodiments. Other embodiments are within the scope of the invention, such as embodiments in which the tip of the swab is 89 degrees, 88 degrees, 87 degrees, 86 degrees, 85 degrees, 80 degrees, 75 degrees, 70 degrees, 60 degrees, 50 degrees, 40 degrees, 30 degrees, 20 degrees, or 10 degrees with respect to the inlet of the mass spectrometer. Other embodiments of tip angle with respect to the inlet of the mass spectrometer include 91 degrees, 92 degrees, 93 degrees 94 degrees, 95 degrees, 100 degrees, 105 degrees, 110 degrees, 120 degrees, 130 degrees, 140 degrees, 150 degrees, 160 degrees, or 170 degrees.

Electrospray was generated using a mixture of acetonitrile, N—N-dimethylformamide, and ethanol (ACN-DMF-EtOH 45:5:50% v/v) as solvent system. The solvent was doped with 250 ng/mL of octyl β-D-glucopyranoside (non-ionic surfactant, ≥98% pure) to facilitate sample now on the probe and 10 ug/mL of the internal standard NAA-$d_3$. Electrospray was initiated after addition of solvent (25 uL/min) directly on the swab tip by applying a high voltage (−6.S kV) to the swab shaft. Full scan mass spectra over the range m/z 700-1000 were acquired in negative ion mode first, then a second acquisition over the mass range m/z 80-200 was performed; after this collision-induced dissociation MS/MS product ion scans were acquired to measure NAA (precursor ion mil 174) and NAA-$d_3$ (precursor ion m/z 177), followed by $MS^3$ product ion scans of 2HG (m/z 147-7129). Blind histopathological evaluation was performed on adjacent tissue sections by an expert neuropathologist. Data were exported from XCalibur 2.0 (Thermo Fisher Scientific) and imported into MATLAB (The Matworks Inc.) for analysis. Receiver operating characteristic (ROC) curve analysis was performed using SPSS v.22 (SPSS Inc. IBM Corp, Chicago, Ill., USA).

Figure 1B:
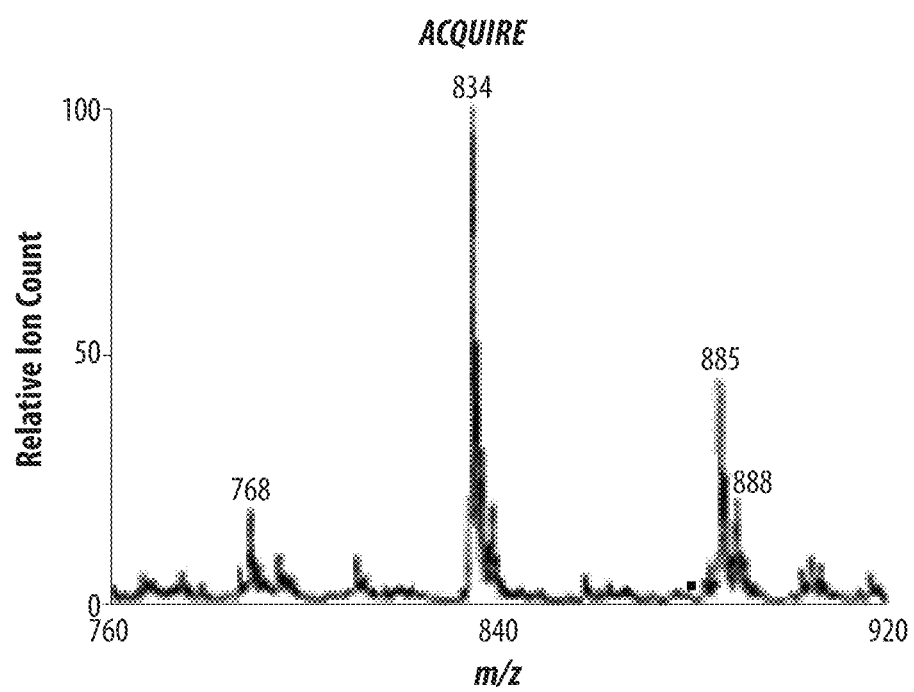

Swab spray MS was performed in such a way as to mimic one foreseeable implementation in which the swab is used to collect tissue in vivo along the surface of the resection cavity, and then immediately placed in front of a mass spectrometer located in the operating room (OR), with analysis occurring within seconds (FIGS. 1A-B). In this study, cryopreserved tissue biopsies served as a proxy for in vivo sampling.

Swab TS MS incorporates a manual user-guided method of collecting tissue with direct MS analysis from the sampling device. This is a strategy to implement chemical pathology into the standard intrasurgical diagnostic consultation. The collection of tissue remotely from the mass spectrometer using a medical swab is a simple process. MS analysis of neurological tissue directly from the sampling device is similarly rapid and straightforward and can be performed inside the OR with no interference with surgical practice. Rapid analysis of tissue should allow assessment of the surgical margin status in multiple locations selected by the neurosurgeon as tumor resection is executed. The diagnostic feedback can provide guidance on further surgical maneuvers to maximize safe tumor resection, especially in proximity of critical anatomical structures. Neurosurgeons are already familiar with the use of swabs and absorbent pads and the device we are describing here to touch neurological tissue would be used no differently. A fit-for-purpose swab design is wanted, however, for optimal performance of the MS analysis. The medical swab we used is commercialized as a class IIA device for surgical invasive transient use (i.e. contact with tissue for less than 60 min). The swab has a sterile mini rayon tip with a fused shape (FIG. 12). It has ideal dimensions to sample minute amounts of tissue by gentle touch and minimize the invasiveness of the sampling procedure. The stiffness and the crevasses in the tip hold the tissue during sample transfer and MS analysis, facilitating analyte extraction and improving electrospray stability. The aluminum handle is conductive and allows the generation of the electrospray directly from the swab upon application of a high voltage.

The average quantity of tissue transferred onto the swab tip for the specimens analyzed in this study was 3.1 mg but acceptable signal-to-noise (>3) ratios for the major peaks in the MS were obtained for as little as 1.0 mg. Table 1 shows the signal-to-noise ratios calculated for each sample for the base peak of the lipid profile mass spectrum (spectrum averaged over 15 seconds of data acquisition). The minute amount of sample collected emphasizes the value of MS analysis directly from the sampling device, viz. no sample loss and high ionization efficiency resulting from minimal solvent consumption (flow rate −25~L per minute). Different solvents (methanol, ACN, DMF, EtOH, dichloromethane, and acetone) were tested during method development based on previous experience with DESI-MS. The system empirically chosen for these analyses (ACN-DMF-EtOH, 45:5:50 v/v %) is the result of an optimization process meant to select a mixture of organic solvents that would provide a chemical fingerprint of the tissue similar to that obtained using DESI-MS (which uses ACN-DMF 50:50 v/v % as solvent system) but one that would also generate an electrospray from the swab tip. The use of the original ACN-DMF DESI solvent was not acceptable because of poor spray behavior observed in the negative ionization mode for swab spray MS.

Figure 7:
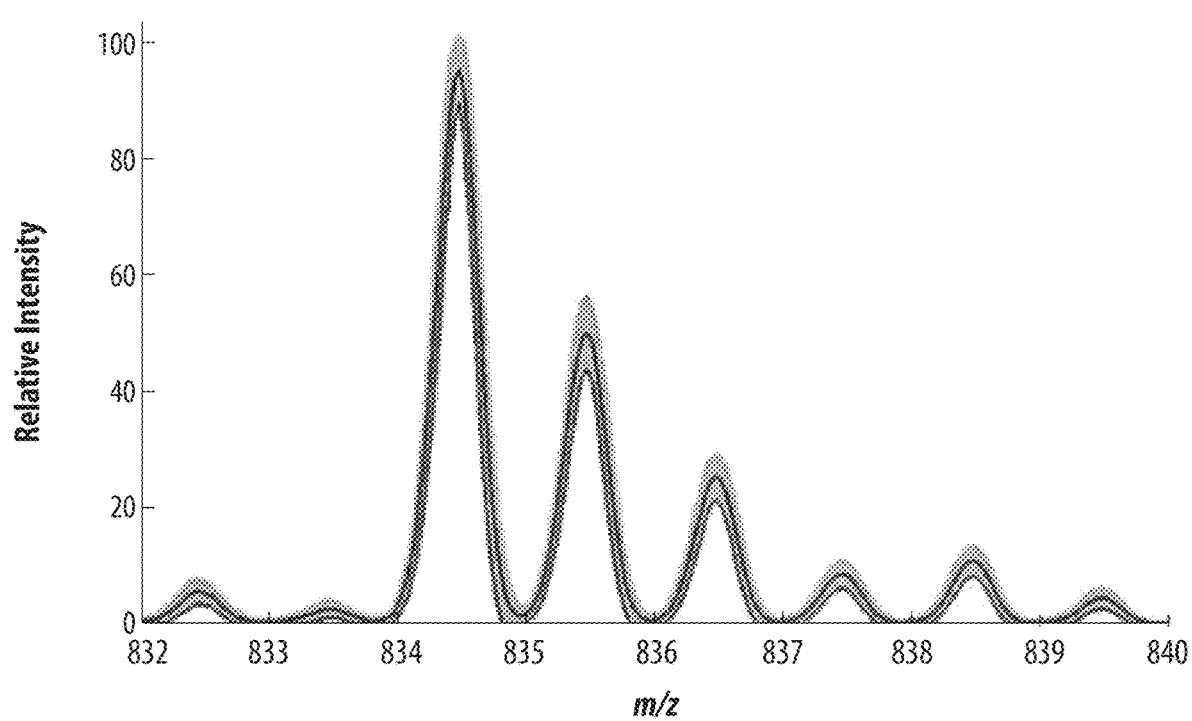
FIG. 7 is a plot of m/z 834.5 (PS 18:0_22:6) average peak with standard deviation. Mean ion intensity denoted by solid line with ±standard deviation illustrated by the shaded area between the dotted lines. Number of scans averaged=1026 over 10 min of data acquisition.
Figure 8A:
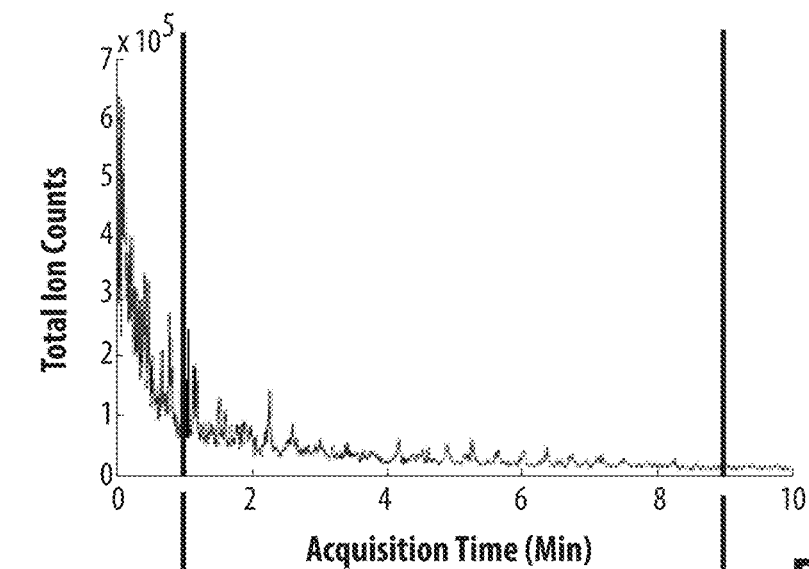
FIG. 8 panels A-C show chemical and pathological diagnosis: grey matter infiltrated with low TCP.
Figure 8B:
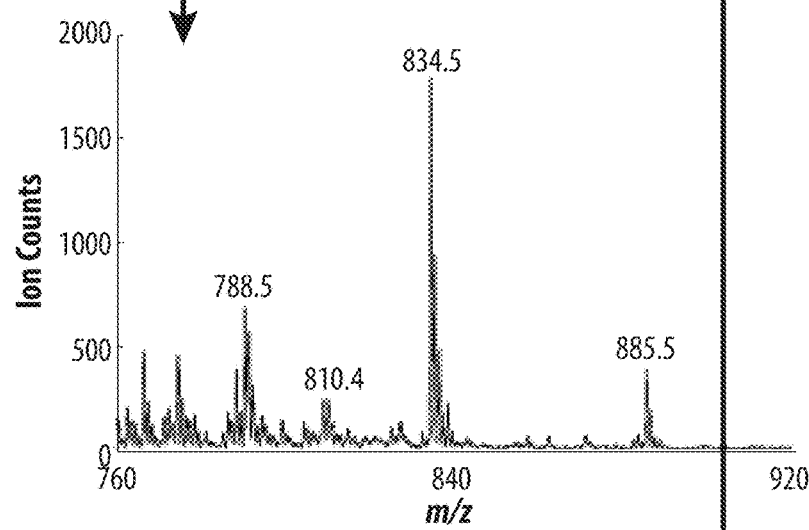
Figure 8C:
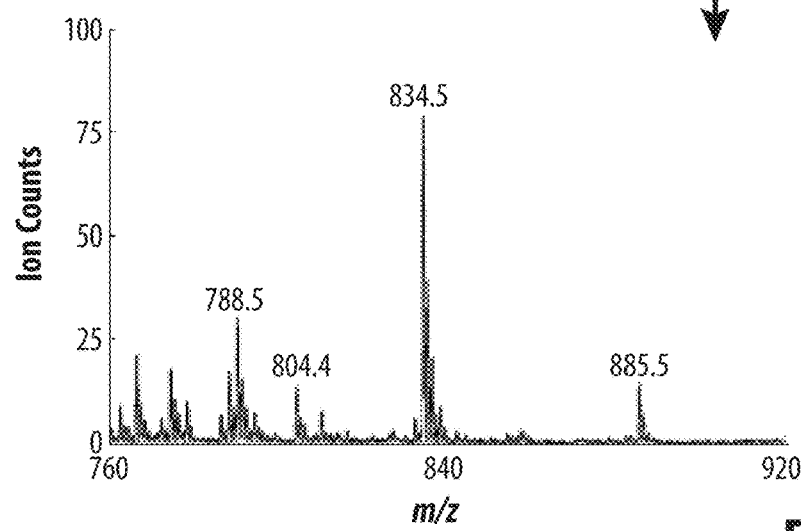

The entire tissue sampled on the swab is interrogated altogether by the constantly-flowing solvent, leading to a chemical profile that is stable over time and represents the average signature arising from the heterogeneous morphological features sampled. As already observed by DESI-MS, the absolute signal intensity changed with the quantity of tissue sampled, as well as with its composition and cellularity. High grade and high density tumor tissue provided less absolute signal compared to low infiltrated tissue, partly due to the presence of calcified, hemorrhagic and necrotic tissue. Note that an internal standard added to the extraction solvent normalizes variations of absolute ion counts due to swab positioning and instability of the electrospray. Importantly, the relative spectral profiles (i.e. relative intensity of ions within a scan) that are used as a diagnostic fingerprint of the tissue were uninfluenced by intensity variations. We monitored the spectral profiles repeated over a total period of ten minutes in several samples of different tissue states and the relative changes of signal intensity were minimal (relative standard deviations <15% for diagnostic ions, FIG. 7). The absolute signal decreased monotonically over time which is typical of a continuous extraction process (FIG. 8 panels A-C).

Figure 2A:
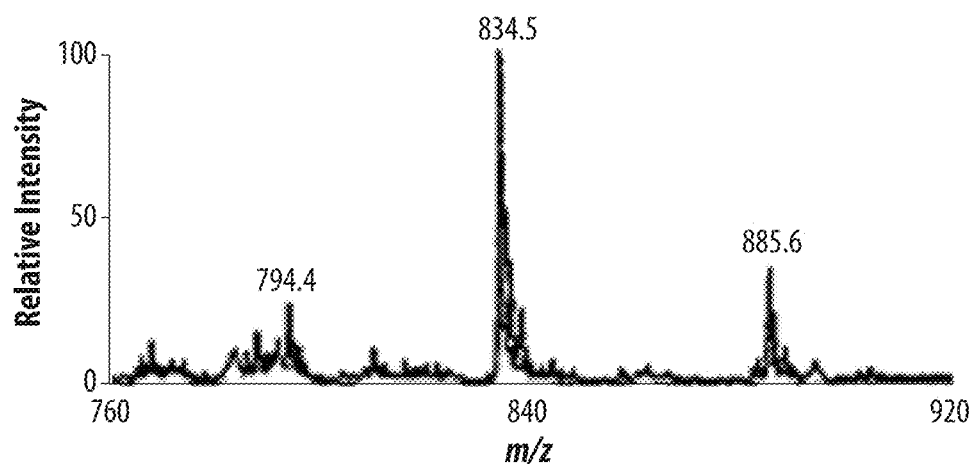
FIG. 2 panels A-C are representative full scan TS mass spectra in negative ion mode over m/z 760-920.
Figure 2B:
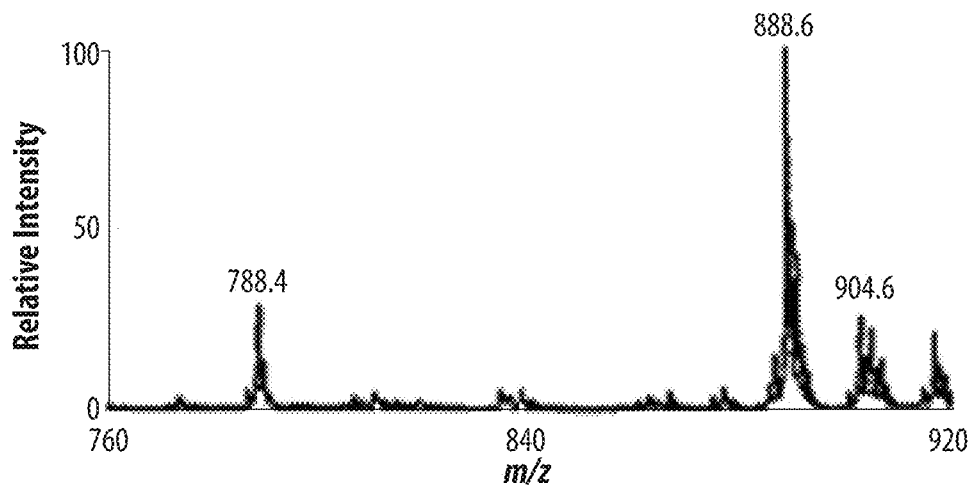
Figure 2C:
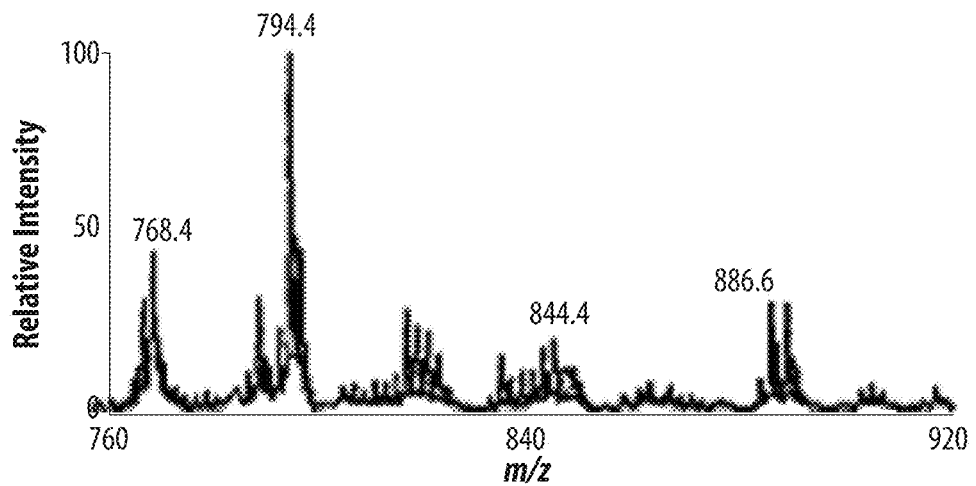
Figure 9A:
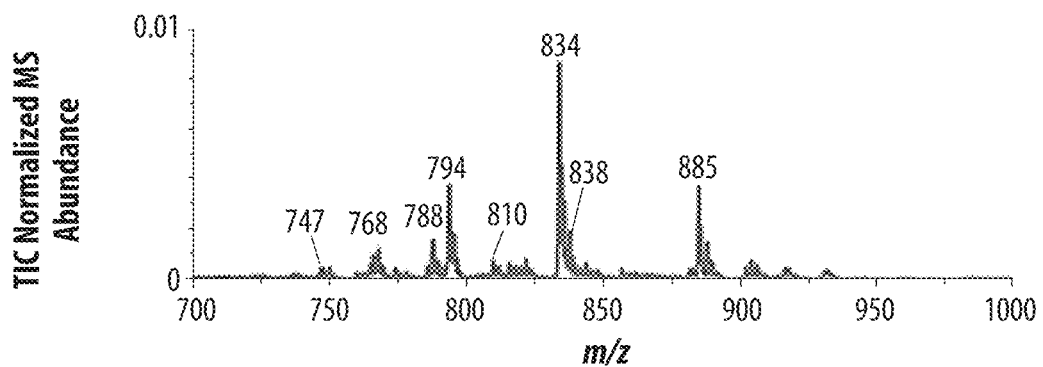
FIG. 9 panels A-C show average DESI-MS lipid (m/z 700-1000) MS profiles for (FIG. 9 panel A) gray matter (N=223), (FIG. 9 panel B) white matter (N=66), and (FIG. 9 panel C) glioma (N=158). Ion intensities are normalized to the total ion count (TIC).
Figure 9B:
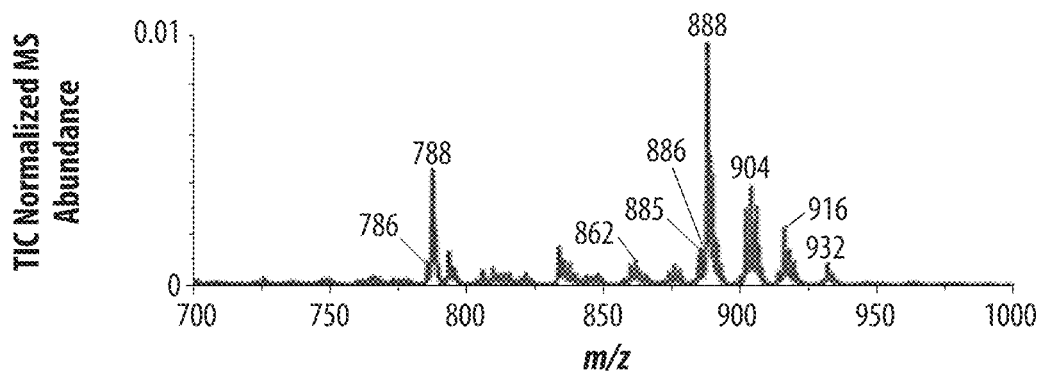
Figure 9C:
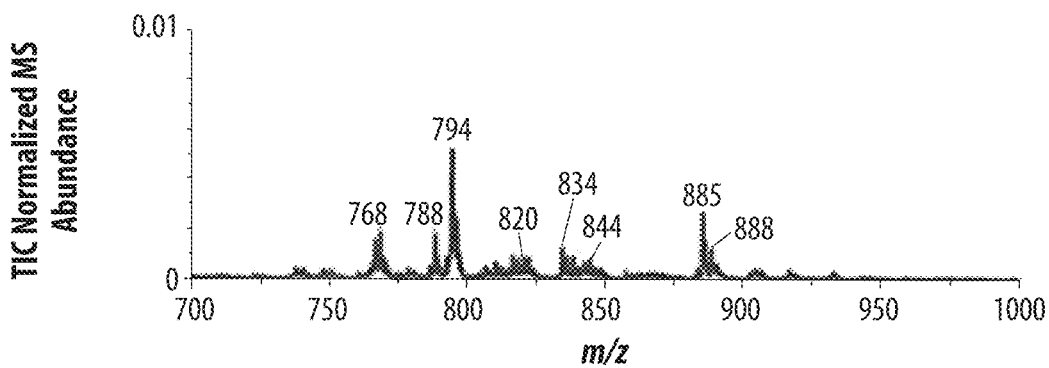
Figure 10A:
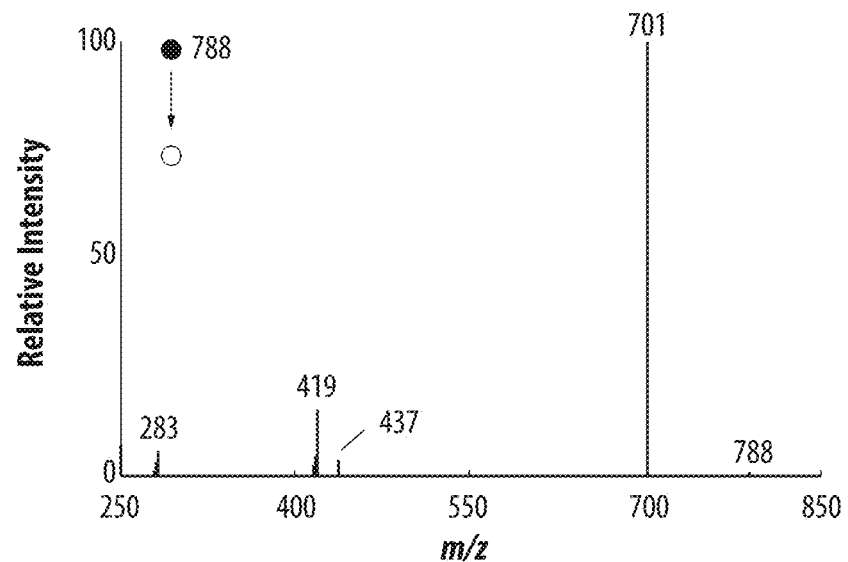
FIG. 10 panels A-B show MS/MS product ion spectra for m/z 788 (FIG. 10 panel A) and m/z 834.
Figure 10B:
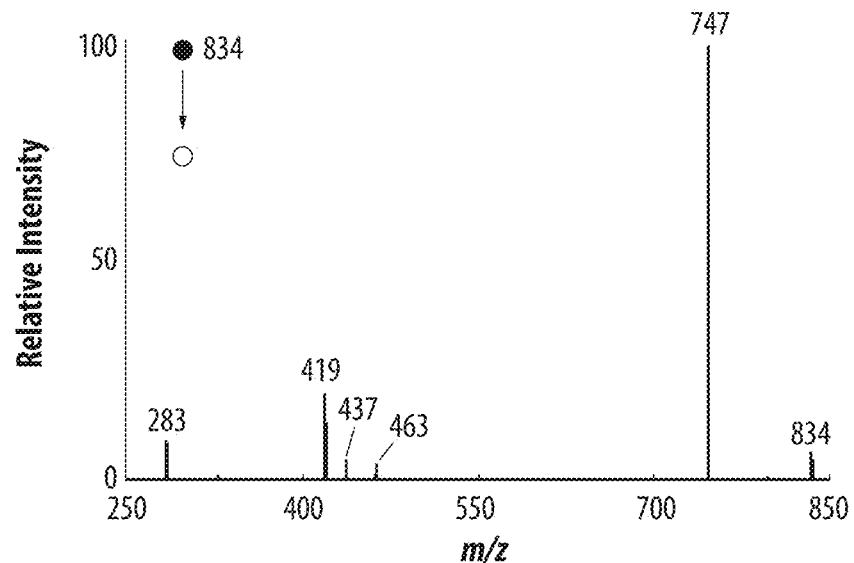

The lipid profiles detected by swab spray MS resembled those detected by DESI-MS (Jarmusch et al., Proc Natl Acad Sci USA 2016; 113:1486-91). They indicated the presence of tumor and could distinguish the type of normal tissue into which the tumor infiltrated, i.e. grey matter and/or white matter. The main MS feature characterizing grey matter is m/z 834.5, the deprotonated ion of phosphatidylserine 40:6 (FIG. 2 panel A). The main MS features characteristic of white matter are m/z 888.6 and 904.5, deprotonated ions for (3-sulfo)GalCer 24:1 and (3'-sulfo)GalCer 24:1(OH) (FIG. 2 panel B). For gliomas the characteristic ions are m/z 768.4, the chlorinated adduct of phosphatidylcholine 32:0, m/z 794.5, chlorinated adduct of phosphatidylcholine 34:1, and m/z 885.5, the deprotonated phosphatidylinositol 38:4 (FIG. 2 panel C). FIG. 9 panels A-C show category spectra acquired by DESI-MS (18) for comparison. High resolution MS and $MS^2$ experiments have been previously recorded using DESI for structural identification (Jarmusch et al. above). These experiments were repeated using swab spray MS and confirmed the structural assignments (FIG. 10 panels A-B). Increased intensity of m/z 810.4, corresponding to phosphatidylserine 38:4 was observed in a few specimens. We attribute it to blood absorption on the swab tip as this lipid is a major membrane constituent of erythrocytes. This interference did not compromise our ability to determine the presence of tumor in the tissue but further evaluation is needed from specimens collected in vivo.

Figure 3:
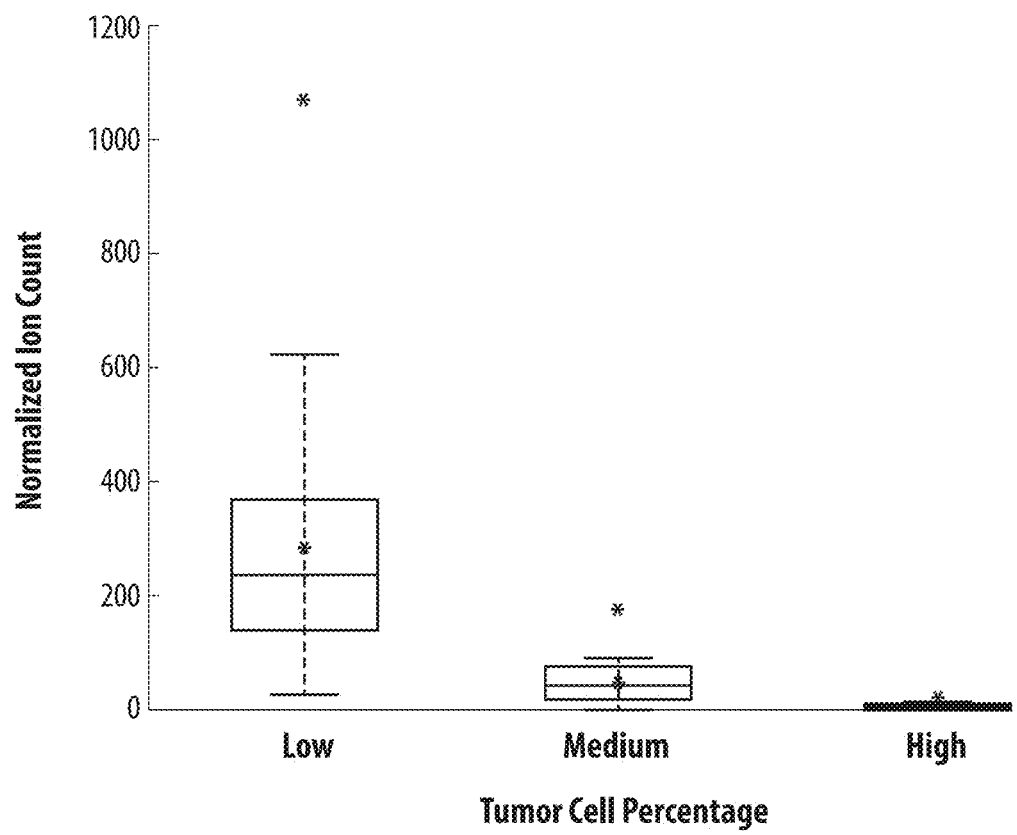
FIG. 3 is a box and whisker plot for NAA abundance in tissue categorized as low <34%, N=24), medium (34-67%, N=12) and high (>67%, N=11) TCP; total N=47. Note, multiple touches from the same specimen were considered as independent measurements as the neuropathologist annotated the presence of heterogeneous areas In the tissue of adjacent sections (Table 51). The ion counts correspond to the signal intensity of the transition m/z 174→114 normalized to the ion counts of the transition m/z 177→116 (the internal standard). The box represents the inter-quartile range with a median line and whiskers at ±1.5 SD. Squares represent the mean value. Circles represent outliers. Zero intensity was assigned to sample #13 in which no NAA signal was detected.
Figure 4A:
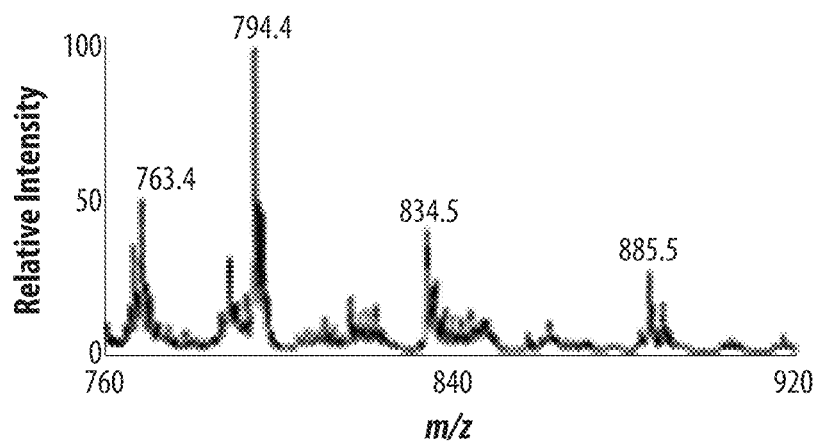
FIG. 4 panels A-I shows sample analysis using swab spray MS.
Figure 4B:
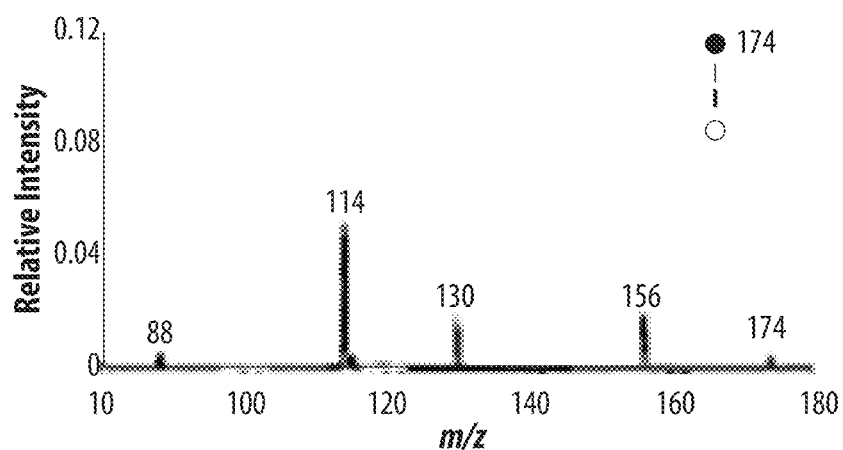
Figure 4C:
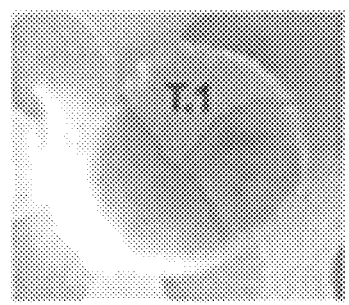
Figure 4D:
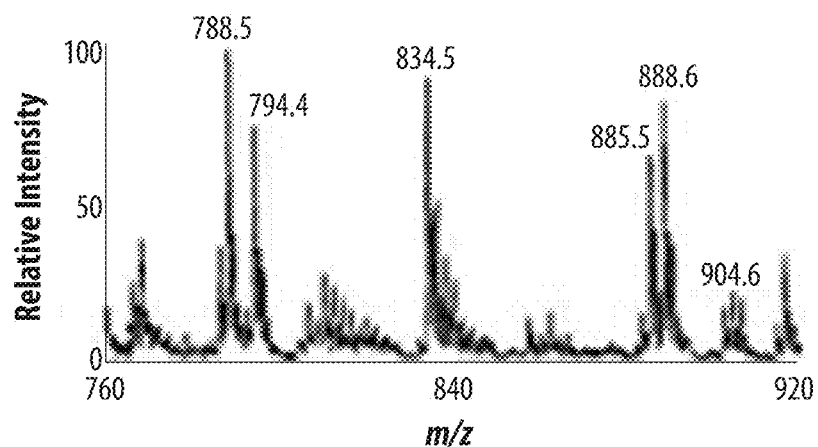
Figure 4E:
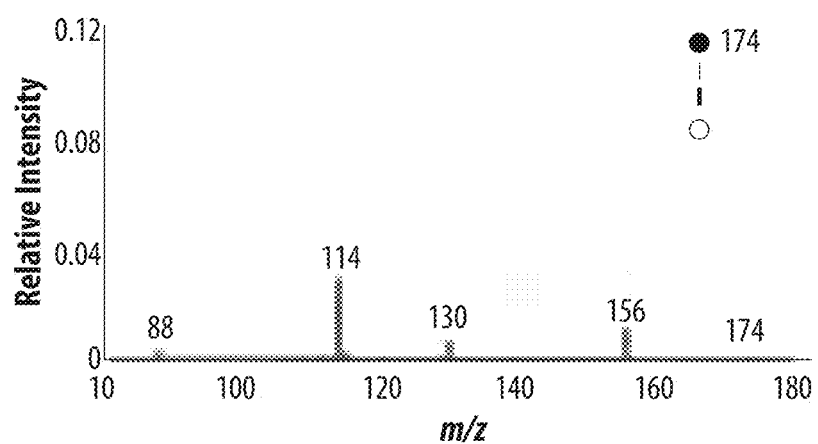
Figure 4F:
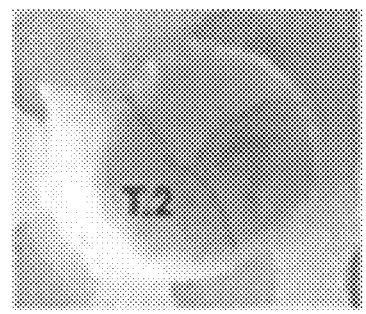
Figure 4G:
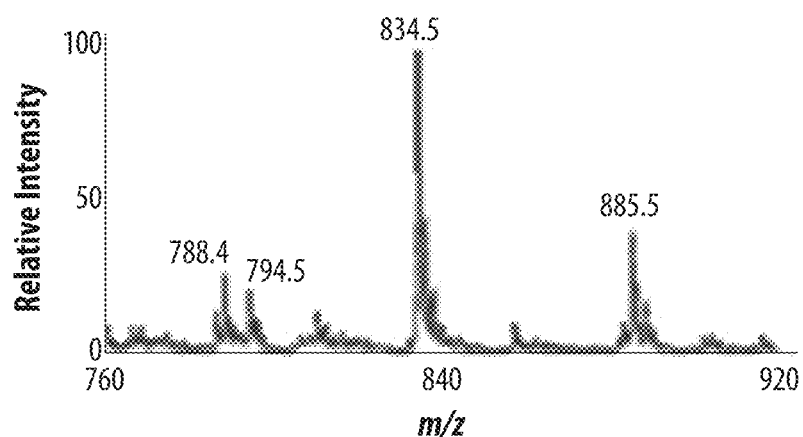
Figure 4H:
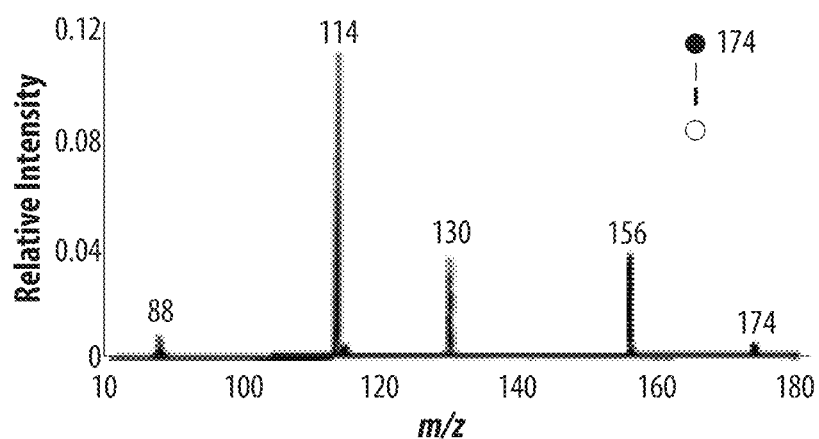
Figure 4I:
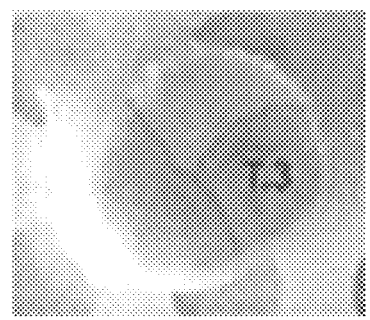

Decreased NAA abundance was observed in swab spray MS as the tumor cell percentage (TCP), i.e. tumor cells relative to normal cells as measured by pathology, increased (FIG. 3). This measurement therefore provides an estimate of tumor infiltration within the tissue, and corroborates prior DESI-MS observations made on tissue and tissue smears (18, 19, 21), as well as literature reports regarding the expression of the biosynthetic enzyme L-aspartate N-acetyltransferase in glioma cells (27). The neuropathologist (EH) categorized the TCP as low (<33%), medium (34-67%), and high (>67%). Estimation of tumor infiltration directly from points of interest along the resection margins can guide tumor excision. Intraoperative DESI-MS measurements showed that variable and even large amounts of residual tumor can be identified at the resection margins even when they appear clear and non-enhanced by postoperative MRI (Pirro et al., Proc Natl Acad Sci USA 2017. DoI: 10.1073/pnas.1706459114, the content of which is incorporated by reference herein in its entirety). In current surgical practice, the amount of residual tumor near the resection margins is not assessed during surgery and several studies have highlighted the limitations and the subjectivity of a practice that relies mainly on preoperative MRI images to judge extent of tumor resection. Intraoperative MS measurements of tumor infiltration can be used to assist and validate the surgeon's decisions, with the overarching goal of maximizing tumor excision to improve surgical outcomes for glioma patients.

We further validated the swab spray MS measurements by quantifying NAA in the same specimens using an independent protocol. Briefly, an adjacent portion of the tissue that was sampled by spray MS was removed and extracted using methanol-water (3:2 v/v). The solution was analyzed by traditional electrospray ionization—triple quadrupole mass spectrometry operated in the multiple reaction monitoring mode. The average normalized signal intensities for FIG. 3 correlated with the average NAA concentrations of 797, 406, and 42 ng/mg for low, medium, and high TCP (30). The subject cohort is limited and as such we do not define diagnostic thresholds; note, however the agreement between independent measurements for validation of NAA's alteration with the increasing faction of tumor cells.

Overall, the changes in the lipid and NAA features in swab spray MS reflect the known complexity of gliomas that can irregularly infiltrate into the surrounding brain parenchyma, as corroborated by pathological examination of the tissue (Table 1). FIG. 4 panel A-I depict an example of such diagnostic changes. Three regions of interest were sampled from case #19. The touch at the first spot (sample #31) showed low abundance of NAA (indicative of high TCP) and a lipid profile indicative of glioma tissue infiltrating grey matter (FIG. 4 panels A-B). The second spot touched (sample #32) showed low abundance of NAA as well but the lipid profile was indicative of glioma invading a mixture of white and grey matter (FIG. 4 panels D and E). The third touch (sample #33) showed higher intensity of NAA (lower tumor infiltration) into prevalently grey matter, as indicated by the lipid profile dominated by m/z 834.5 (FIG. 4 panels G and H). Pathological examinations matched with the swab spray MS results (Table 1).

The oncometabolite 2HG accumulates in glioma tissue carrying mutations of the IDH gene, the presence of which is favorably prognostic (Jarmusch et al., Proc Natl Acad Sci USA 2016; 113:1486-91; and Xu et al., Cancer Cell 2011; 19:17-30, the content of each of which is incorporated by reference herein in its entirety). IDH mutation status is normally assessed postoperatively as it relies on laborious immunohistochemistry assays on biopsied tissue; however, its intraoperative assessment via MS measurement of 2HG could influence surgical decisions. An increasing body of evidence is showing that more aggressive resection of IDH-mutant gliomas improves overall and progression-free survival, while more aggressive resection of wild-type tumors does not. Furthermore, the assessment of IDH mutation is required for tumor diagnosis, following the 2016 WHO diagnostic criteria for central nervous system tumors. Intraoperative testing could benefit neuropathologists as means to provide more accurate diagnostic consultation.

Figure 5A:
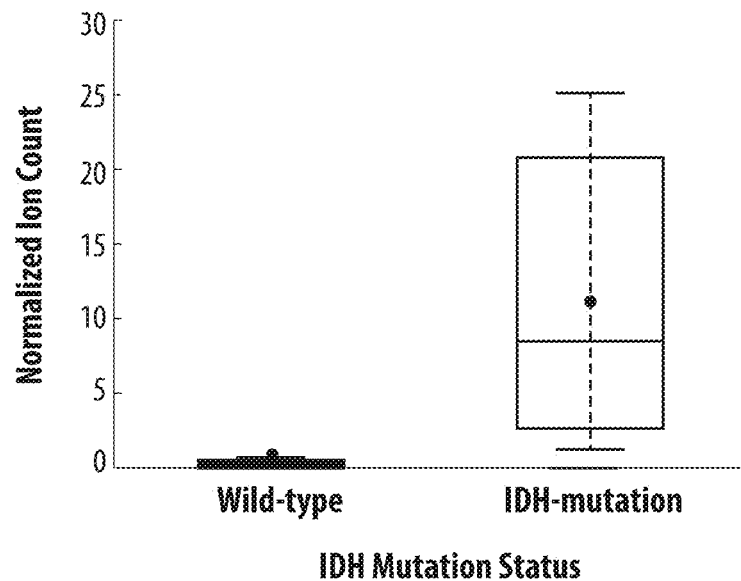
FIG. 5 panel A is a box and whisker plot for 2HG in tissue analyzed by swab spray MS. Wild-type, N=21; IDH-mutant gliomas, N=8. The ion counts correspond to the signal intensity of the transition m/z 147→129→101 normalized to the ion counts of the transition m/z 177→116 for the internal standard. The box represents the interquartile range with a median line and whiskers at ±1.S SD. Squares represent the mean value.
Figure 5B:
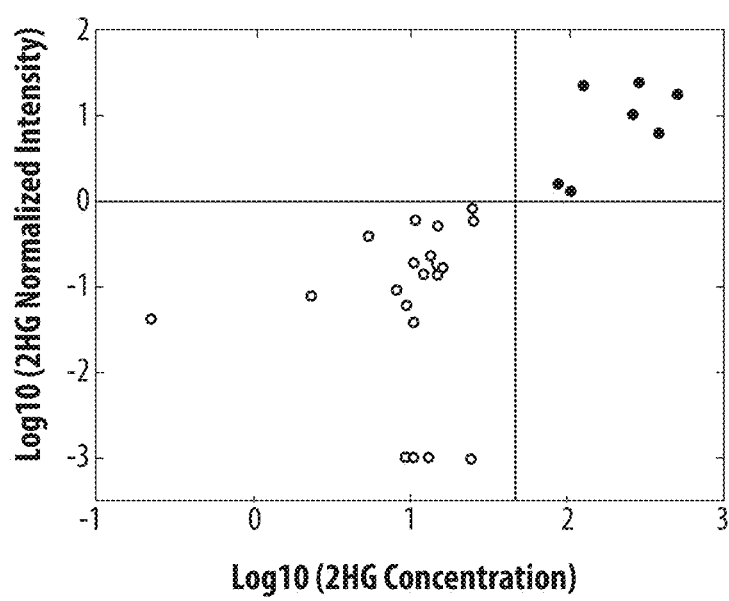
Figure 11:
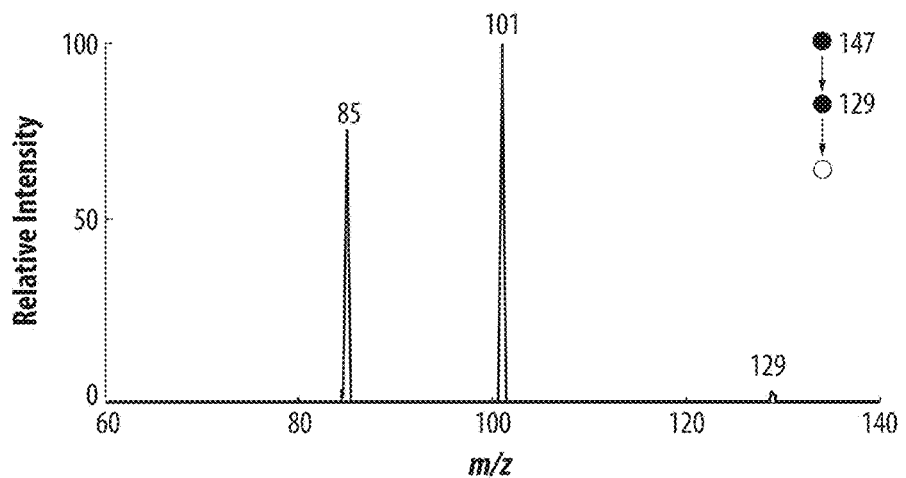
FIG. 11 shows sequential product ion scan for 2HG from case #16, IDH-mutant glioma. Fragmentation of 2HG matches previously reported pattern detected by DESI-MS (17, 19). The fragmentation pattern was also matched against a certified analytical standard.

We detected a 50-fold increase in the average 2HG normalized signal intensity between wild-type gliomas and IDH-mutant gliomas (FIG. 5 panel A). A wide range in 2HG signal intensity was detected for the IDH-mutant gliomas and can be attributed to differences in tissue cellularity and the known heterogeneity of tumor density in the samples (low to high). Note, that the IDH mutation was provided per specimen from the tissue bank in dichotomous type (immunoreactive, non-immunoreactive). IDH mutation was assessed using immunohistochemistry assays on an adjacent portion of the tissue. We averaged the 2HG measurements of multiple touches from the same specimens to avoid bias due to sample size (N=29). The possibility that other compounds give ions that interfere with the signal for 2HG in the full scan mass spectrum led us to increase specificity for 2HG by using the $MS^3$ collision induced dissociation sequence m/z 147→129→101. A product ion scan spectrum from an IDH-mutant glioma is shown in FIG. 11. The logarithmic signal intensity of 2HG equal to 1.02 is a cut-off that discriminates this set of IDH-mutant gliomas and wild-type gliomas with 100% accuracy (using receiver operating characteristic curve analysis). This observation was confirmed by quantitation of 2HG in adjacent tissue of the same specimens, performed as described above for NAA (N=28; case #29 was excluded because of insufficient tissue quantity to perform both experiments). A cut-off of 45 ng/mg for the 2HG concentration was found to discriminate IDH-mutant and wild-type tumors. There is complete accordance between the relative swab TS-MS measurements and the quantitative measurements by ESI-MS and consequently between diagnosis (FIG. 5 panel B). There is also agreement with intrasurgical DESI measurements recently reported.

The data herein demonstrate the feasibility of obtaining diagnostic information by touching tissue using a medical swab followed by direct MS analysis from the sampling device. Rapid analysis and minimally invasive sampling are major advantages of swab spray MS. Spectra obtained from swab spray MS recapitulate previously reported DESI-MS spectra and pathology. In addition to providing information as to the disease state of the tissue, i.e. normal or tumor, oncometabolites can be detected to provide estimates of tumor infiltration, i.e., from NAA, and assessment of IDH mutation status, i.e. from 2HG. The former is of utmost importance when attempting to maximize glioma resection; the latter is clinically informative and a strong prognostic marker. We envision neurosurgeons, contending with resection decisions, to utilize this tool for collection of tissue in points of interest, along the surface of the resection cavity, in which further evaluation and testing is desired. The rapid chemical pathological feedback can guide decision-making and potentially maximize tumor resection, an outcome associated with better patient prognosis.

Biomarkers of Disease

As discussed above, the biomarker chosen is immaterial to the operation of the invention as long as the marker is associated with the disease for which screening is being conducted. Some biomarkers that have been associated with disease include nucleic acid markers (including but not limited to K-ras, K-ras2, APC, DCC, TP53, PRC I, NUSAPI, CAPZ, PFKP, EVER1, FLT1, ESPL I, AKAP2, CDC45L, RAMP, SYNGR2, NDRG1, ZNF533, and hypermethylated nucleic acid), proteins and peptides, carbohydrates, sugars, glycans, lipids, hormones (e.g., antidiuretic hormone (ADH), Adrenocorticotrophic hormone (ACTH), growth hormone (GH), follicle stimulating hormone (FSH), luteinizing hormone (LH), estrogen (estradiol, estrone, estriol), progesterone, testosterone, dihydrotestosterone (DHT), inhibin, somatotropin, dehydroepiandrostenedione (DHEA), somatostatin, glucagon, insulin, thyrotropin, thyroid stimulating hormone (TSH), thyroxin, parathyroid hormone, corticotropin, cortisol, corticosteron, aldosterone, epinephrine, norepinephrine, prolactin, vasopressin, oxytocin, melanocyte stimulating hormone (MSH)), growth factors (e.g., granulocyte-colony stimulating factor (G-CSF), granulocyte-macrophage colony stimulating factor (GM-CSF), nerve growth factor (NGF), neurotrophins, platelet-derived growth factor (PDGF), erythropeitin (EPO), thrmobopoeitin (TPO), myostatin (GDF-8), growth differentiation factor (GDF-9), basic fibroblast growth factor (bFGF or FGF2), acidic fibroblast growth factor, fibroblast growth factor receptor 3 (FGFR3), epidermal growth factor (EGF), hepatocyte growth factor (HGF), human stem cell factor (SCF), tumor necrosis factor (TNF), tumor necrosis factor-β (TNF-β), tumor necrosis factor-α (TNF-α), vascular endothelial growth factor (VEGF), transforming growth factor-β (TGF-β), transforming growth factor-α (TGF-α), insulin-like growth factor-I (IGF-II), insulin-like growth factor-II (IGF-II), and colony stimulating factor (CSF)), cytokines (e.g., IL-1α, IL-1β, IL-2, IL-3, IL-4, IL-5, IL-6, IL-7, IL-8, IL-9, IL-10, IL-11, IL-12, IL-13, IFN-α, IFN-β, and IFN-γ), proteins (e.g., Matrix metalloproteinases (MMPs) such as MMP2, MMP9, neutrophil gelatinase-associated lipocalin (NGAL), MMP/NGAL complex, thymosin β15, thymosin β16, collagen like gene (CLG) product, prohibitin, glutathione-S-transferase, beta-5-tubulin, ubiquitin, tropomyosin, Cyr61, cystatin B, chaperonin 10, profilin, Alpha-fetoprotein, Carcinoembryonic antigen, Epidermal growth factor receptor, Kallikrein 3 (prostate specific antigen), Vascular endothelial growth factor A, VEGF, Albumin, CA 125, Calcitonin, Chromogranin A (parathyroid secretory protein 1), Corticotropin-lipotropin contains ACTH, Estrogen receptor 1, Gastrin, Progesterone receptor, Prolactin, S100 alpha chain, Somatostatin, Thyroglobulin, V-erb-b2, Her2/neu, Antigen identified by monoclonal antibody Ki-67, B-cell CLUlymphoma 2, BCL2-associated X protein, Beta-2-microglobulin, Breast cancer 1 early onset, BRCA1, CA 15.3, CA 19.9, Cadherin 1 type 1 E-cadherin (epithelial), Caspase 3, CD44 antigen, Cellular tumor antigen p53, Coagulation factor II, prothrombin, Colony stimulating factor 2 (granulocyte-macrophage), Colony stimulating factor 3 (granulocyte), C-reactive protein, Cyclin D1, Cyclin-dependent kinase inhibitor 1, p21, Erythropoietin, Fibrinogen alpha/alpha-E chain, Follicle-stimulating hormone, Gamma enolase, Insulin, Interferon gamma, Interleukin 2, Interleukin 6, k-ras, Neprilysin, CD10, Transferrin, Trypsin, Tumor necrosis factor (TNF-alpha), Tumor necrosis factor receptor superfamily member 6, fas, Von Willebrand Factor, Chemokine, Chitinase-3 like protein 1, YKL-40, Choriogonadotropin beta chain, Colony stimulating factor 1 (macrophage), Haptoglobin-1, Hepatocyte growth factor, Inhibin, Interferon-alpha/beta receptor alpha chain, Interferon-alpha/beta receptor beta chain, Kallikrein 10, Kallikrein 11, Kallikrein 6, Matrix metalloproteinase 3, ADAM-12, Small inducible cytokine A21 (CCL21) soluble IL-2R alpha, Somatotropin growth factor, growth hormone, Breast cancer 2 early onset, BRCA2, Catenin Beta 1, Cathepsin D, CD15, Desmin, DNA-(apurinic or apyrimidinic site) lyase, APEX, Lutropin beta chain, Luteinizing hormone, Parathyroid Hormone, Proliferating cell nuclear antigen, Tumor necrosis factor ligand superfamily member 8 (CD30 ligand), V-myc myelocytomatosis viral oncogene homolog (avian), Tumor necrosis factor ligand superfamily member 8 (CD30), 17beta-Hydroxysteroid dehydrogenase type 1 (17HSD1), Acid phosphatase prostate, Adrenomedullin, Aldolase A, bone-specific Alkaline phosphatase, Alkaline phosphatase, placental type, Alpha-1-acid glycoprotein 1, orosomucoid, Alpha-1-antitrypsin, alpha-2-H S-glycoprotein, Alpha-2-macroglobulin, Alpha-lactalbumin, Angiogenin ribonuclease RNase A family 5, Angiopoietin 1, Angiopoietin 2, Antileukoproteinase 1, SLPI, Apolipoprotein A1, Apolipoprotein A-II, Apolipoprotein C-1, Apolipoprotein C-III, Bone sialoprotein II, Brain-derived neurotrophic factor, Breast cancer metastasis-suppressor 1, CA 27.29, CA 72-4, Cathepsin B, CC chemokine 4, HCC-4, CD44 variant V5 soluble, Ceruloplasmin, Cervical cancer 1 protooncogene protein p40, Chemokine (C-C motif) ligand 4 Small inducible cytokine A4 (CCL4), MIP-1-beta, Claudin-3, Claudin-4, Clusterin, Coagulation factor III, Coagulation factor XIII A chain, Coagulation factor XIII B chain, Collagen I c-terminal telopeptide, Complement component 3, Complement component 4, Complement component 7, Complement factor H related protein, Cyclin-dependent kinase 6, Cyclooxygenase-2, Cystatin A, Cystatin B, Cystatin C, Cytokeratin 8, Diazepam binding inhibitor, Endoglin, Endothelin 1, Epidermal growth factor, E-selectin, Ferritin H, Fibroblast growth factor 2 (basic), Fibronectin 1, Flt-3 ligand, Fms-related tyrosine kinase 1, VEGFRI, Follistatin, Fructose-bisphosphate aldolase B, Fructose-bisphosphate aldolase C, Geminin, Glucose-6-phosphate isomerase, Glypican-3, n-terminal, Growth arrest and DNA-damage-inducible alpha, Immunosuppressive acidic protein, Insulin-like growth factor 1 (somatomedin C), Insulin-like growth factor 2 (somatomedin A), Insulin-like growth factor binding protein 1, Insulin-like growth factor binding protein 2, Insulin-like growth factor binding protein 3, Intercellular Adhesion Molecule 1, Interferon alpha 1, Interleukin 1 alpha, Interleukin 1 beta, Interleukin 10, Interleukin 12A, Interleukin 16, Interleukin 5, Interleukin 6 receptor, Interleukin 6 signal transducer, Interleukin 7, Interleukin 8, Interleukin 9, Interleukin-1 receptor antagonist protein, IRAP, Kallikrein 14 (hK14), Kallikrein 2 prostatic, Kallikrein 5, Kallikrein 7, Kallikrein 8, Kallikrein 18, Kallikrein 8, Keratin 18, Keratin, type I cytoskeletal 19, cytokeratin 19, Kit ligand, Lactotransferrin, Leptin, L-selectin, Luteinizing hormone-releasing hormone receptor, Mac-2 Binding Protein 90K, Mammaglobin B, Mammary Serum, Antigen, Mast/stem cell growth factor receptor, Melanoma-inhibiting activity, Membrane cofactor protein, CD46 antigen, Mesothelin, Midkine, MK-1 protein, Ep-CAM, Myoblast determination protein 1, Nerve growth factor beta, Netrin-1, Neuroendocrine secretory protein-55, Neutrophil defensin 1, Neutrophil defensin 3, Nm23-H 1, OVX1, OX40, p65 oncofetal protein, Pancreatic secretory trypsin inhibitor, TATI, Parathyroid hormone-related protein, Pcaf, P300/CBP-associated factor, Pepsinogen-1, Placental specific tissue protein 12 Plasma retinol-binding protein, Plasminogen (Contains Angiostatin), Platelet endothelial cell adhesion molecule, PECAM-1, Platelet factor 4, Platelet-derived growth factor beta polypeptide, Platelet-derived growth factor receptor alpha polypeptide, Pregnancy zone protein, Pregnancy-associated plasma protein-A, Prostate secretory protein PSP94, P-selectin, PSP94 binding protein, Pyruvate kinase, isozymes M1/M2, Riboflavin carrier protein, 100 beta chain, Secreted phosphoprotein 1, osteopontin, Serine (or cysteine) proteinase inhibitor Glade B, maspin, Serine (or cysteine) proteinase inhibitor clade E, PAI-1, Serum amyloid alpha-1, Serum paraoxonase/arylesterase 1, Small inducible cytokine A14 CCL14, Small inducible cytokine A18(CCL18), MIP-4, Small inducible cytokine A2(CCL2), Small inducible cytokine A3(CCL3), Macrophage inflammatory protein 1-alpha, Small inducible cytokine B5(CXCL5), Squamous cell carcinoma antigen 1, Squamous cell carcinoma antigen 2, Survivin, Syndecan-1, synuclein-gamma, TEK tyrosine kinase endothelial, Tie-2, Tenascin, Tetranectin, TGF-beta receptor type III, Thiredoxin reductase 1, Thrombopoietin, Thrombopoietin 1, Thymidin kinase, Tissue inhibitor of metalloproteinase1, Tissue inhibitor of metalloproteinase2, Tissue-type plasminogen activator, tPA, Transferrin receptor (p90 CD71), Transforming growth factor alpha, Transforming growth factor beta 1, transthyretin, Tropomyosin 1 alpha chain (Alpha-tropomyosin), Tumor necrosis factor (ligand) superfamily member 5, CD154, Tumor necrosis factor (ligand) superfamily member 6, Fas ligand, Tumor necrosis factor ligand superfamily member 13B, TALL-1, Tumor necrosis factor receptor superfamily member 11 B, osteoprotegerin, Tumor necrosis factor receptor superfamily member 1A p60 TNF-RI p55 CD120a, TNFR1, Tumor necrosis factor receptor superfamily member 1B, TNFR2, Urokinase plasminogen activator surface receptor, U-PAR, Vascular cell adhesion molecule 1, Vascular endothelial growth factor receptor 2, Vasoactive intestinal peptide, VEGF(165)b, Vitamin K dependent protein C, Vitronectin, and X box binding protein-1), or any combination thereof.

In certain embodiments, the disease is cancer. Biomarkers that have been associated with types of cancers are well known in the art.

Biomarkers associated with development of breast cancer are shown in Erlander et al. (U.S. Pat. No. 7,504,214), Dai et al. (U.S. Pat. Nos. 7,514,209 and 7,171,311), Baker et al. (U.S. Pat. Nos. 7,056,674 and 7,081,340), Erlander et al. (US 2009/0092973). The contents of the patent application and each of these patents are incorporated by reference herein in their entirety. Exemplary biomarkers that have been associated with breast cancer include: ErbB2 (Her2); ESR1; BRCA1; BRCA2; p53; mdm2; cyclin1; p27; B_Catenin; BAG1; BIN1; BUB1; C20_orf1; CCNB1; CCNE2; CDC20; CDH1; CEGP1; CIAP1; cMYC; CTSL2; DKFZp586M07; DR5; EpCAM; EstR1; FOXM1; GRB7; GSTM1; GSTM3; HER2; HNRPAB; ID1; IGF1R; ITGA7; Ki_67; KNSL2; LMNB1; MCM2; MELK; MMP12; MMP9; MYBL2; NEK2; NME1; NPD009; PCNA; PR; PREP; PTTG1; RPLPO; Src; STK15; STMY3; SURV; TFRC; TOP2A; and TS.

Biomarkers associated with development of cervical cancer are shown in Patel (U.S. Pat. No. 7,300,765), Pardee et al. (U.S. Pat. No. 7,153,700), Kim (U.S. Pat. No. 6,905,844), Roberts et al. (U.S. Pat. No. 6,316,208), Schlegel (US 2008/0113340), Kwok et al. (US 2008/0044828), Fisher et al. (US 2005/0260566), Sastry et al. (US 2005/0048467), Lai (US 2008/0311570) and Van Der Zee et al. (US 2009/0023137). The contents of each of the articles, patents, and patent applications are incorporated by reference herein in their entirety. Exemplary biomarkers that have been associated with cervical cancer include: SC6; SIX1; human cervical cancer 2 protooncogene (HCCR-2); p27; virus oncogene E6; virus oncogene E7; $p16^{INK4A}$; Mcm proteins (such as Mcm5); Cdc proteins; topoisomerase 2 alpha; PCNA; Ki-67; Cyclin E; p-53; PAI1; DAP-kinase; ESR1; APC; TIMP-3; RAR-β; CALCA; TSLC1; TIMP-2; DcR1; CUDR; DcR2; BRCA1; p15; MSH2; Rassf1A; MLH1; MGMT; SOX1; PAX1; LMX1A; NKX6-1; WT1; ONECUT1; SPAG9; and Rb (retinoblastoma) proteins.

Biomarkers associated with development of vaginal cancer are shown in Giordano (U.S. Pat. No. 5,840,506), Kruk (US 2008/0009005), Hellman et al. (Br J Cancer. 100(8): 1303-1314, 2009). The contents of each of the articles, patents, and patent applications are incorporated by reference herein in their entirety. Exemplary biomarkers that have been associated with vaginal cancer include: pRb2/p130 and Bcl-2.

Biomarkers associated with development of brain cancers (e.g., glioma, cerebellum, medulloblastoma, astrocytoma, ependymoma, glioblastoma) are shown in D' Andrea (US 2009/0081237), Murphy et al. (US 2006/0269558), Gibson et al. (US 2006/0281089), and Zetter et al. (US 2006/0160762). The contents of each of the articles and patent applications are incorporated by reference herein in their entirety. Exemplary biomarkers that have been associated with brain cancers include: epidermal growth factor receptor (EGFR); phosphorylated PKB/Akt; EGFRvIII; FANCI; Nr-CAM; antizyme inhibitor (AZI); BNIP3; and miRNA-21.

Biomarkers associated with development of renal cancer are shown in Patel (U.S. Pat. No. 7,300,765), Soyupak et al. (U.S. Pat. No. 7,482,129), Sahin et al. (U.S. Pat. No. 7,527,933), Price et al. (U.S. Pat. No. 7,229,770), Raitano (U.S. Pat. No. 7,507,541), and Becker et al. (US 2007/0292869). The contents of each of the articles, patents, and patent applications are incorporated by reference herein in their entirety. Exemplary biomarkers that have been associated with renal cancers include: SC6; 36P6D5; IMP3; serum amyloid alpha; YKL-40; SC6; and carbonic anhydrase IX (CA IX).

Biomarkers associated with development of hepatic cancers (e.g., hepatocellular carcinoma) are shown in Horne et al. (U.S. Pat. No. 6,974,667), Yuan et al. (U.S. Pat. No. 6,897,018), Hanausek-Walaszek et al. (U.S. Pat. No. 5,310,653), and Liew et al. (US 2005/0152908). The contents of each of the articles, patents, and patent applications are incorporated by reference herein in their entirety. Exemplary biomarkers that have been associated with hepatic cancers include: Tetraspan NET-6 protein; collagen, type V, alpha; glypican 3; pituitary tumor-transforming gene 1 (PTTG1); Galectin 3; solute carrier family 2, member 3, or glucose transporter 3 (GLUT3); metallothionein 1L; CYP2A6; claudin 4; serine protease inhibitor, Kazal type I (SPINK1); DLC-1; AFP; HSP70; CAP2; glypican 3; glutamine synthetase; AFP; AST and CEA.

Biomarkers associated with development of gastric, gastrointestinal, and/or esophageal cancers are shown in Chang et al. (U.S. Pat. No. 7,507,532), Bae et al. (U.S. Pat. No. 7,368,255), Muramatsu et al. (U.S. Pat. No. 7,090,983), Sahin et al. (U.S. Pat. No. 7,527,933), Chow et al. (US 2008/0138806), Waldman et al. (US 2005/0100895), Goldenring (US 2008/0057514), An et al. (US 2007/0259368), Guilford et al. (US 2007/0184439), Wirtz et al. (US 2004/0018525), Filella et al. (Acta Oncol. 33(7):747-751, 1994), Waldman et al. (U.S. Pat. No. 6,767,704), and Lipkin et al. (Cancer Research, 48:235-245, 1988). The contents of each of the articles, patents, and patent applications are incorporated by reference herein in their entirety. Exemplary biomarkers that have been associated with gastric, gastrointestinal, and/or esophageal cancers include: MH15 (Hn1L); RUNX3; midkine; Chromogranin A (CHGA); Thy-1 cell surface antigen (THY1); IPO-38; CEA; CA 19.9; GroES; TAG-72; TGM3; HE4; LGALS3; IL1RN; TRIP13; FIGNL1; CRIP1; S100A4; EXOSC8; EXPI; CRCA-1; BRRN1; NELF; EREG; TMEM40; TMEM109; and guanylin cyclase C.

Biomarkers associated with development of ovarian cancer are shown in Podust et al. (U.S. Pat. No. 7,510,842), Wang (U.S. Pat. No. 7,348,142), O'Brien et al. (U.S. Pat. Nos. 7,291,462, 6,942,978, 6,316,213, 6,294,344, and 6,268,165), Ganetta (U.S. Pat. No. 7,078,180), Malinowski et al. (US 2009/0087849), Beyer et al. (US 2009/0081685), Fischer et al. (US 2009/0075307), Mansfield et al. (US 2009/0004687), Livingston et al. (US 2008/0286199), Farias-Eisner et al. (US 2008/0038754), Ahmed et al. (US 2007/0053896), Giordano (U.S. Pat. No. 5,840,506), and Tchagang et al. (Mol Cancer Ther, 7:27-37, 2008). The contents of each of the articles, patents, and patent applications are incorporated by reference herein in their entirety. Exemplary biomarkers that have been associated with ovarian cancer include: hepcidin; tumor antigen-derived gene (TADG-15); TADG-12; TADG-14; ZEB; PUMP-1; stratum corneum chymotrytic enzyme (SCCE); NES-1; µPA; PAI-2; cathepsin B; cathepsin L; ERCC5; MMP-2; pRb2/p130 gene; matrix metalloproteinase-7 (MMP-7); progesterone-associated endometrial protein (PALP); cancer antigen 125 (CA125); CTAP3; human epididymis 4 (HL4); plasminogen activator urokinase receptor (PLAUR); MUC-1; FGF-2; cSHMT; Tbx3; utrophin; SLPI; osteopontin (SSP1); mesothelin (MSLN); SPON1; interleukin-7; folate receptor 1; and claudin 3.

Biomarkers associated with development of head-and-neck and thyroid cancers are shown in Sidransky et al. (U.S. Pat. No. 7,378,233), Skolnick et al. (U.S. Pat. No. 5,989,815), Budiman et al. (US 2009/0075265), Hasina et al. (Cancer Research, 63:555-559, 2003), Kebebew et al. (US 2008/0280302), and Ralhan (Mol Cell Proteomics, 7(6): 1162-1173, 2008). The contents of each of the articles, patents, and patent applications are incorporated by reference herein in their entirety. Exemplary biomarkers that have been associated with head-and-neck and thyroid cancers include: BRAF; Multiple Tumor Suppressor (MTS); PAI-2; stratifin; YWHAZ; S100-A2; S100-A7 (psoriasin); S100-A11 (calgizarrin); prothymosin alpha (PTHA); L-lactate dehydrogenase A chain; glutathione S-transferase Pi; APC-binding protein EB1; fascin; peroxiredoxin2; carbonic anhydrase 1; flavin reductase; histone H3; ECM1; TMPRSS4; ANGPT2; T1MP1; LOXL4; p53; IL-6; EGFR; Ku70; GST-pi; and polybromo-1D.

Biomarkers associated with development of colorectal cancers are shown in Raitano et al. (U.S. Pat. No. 7,507,541), Reinhard et al. (U.S. Pat. No. 7,501,244), Waldman et al. (U.S. Pat. No. 7,479,376); Schleyer et al. (U.S. Pat. No. 7,198,899); Reed (U.S. Pat. No. 7,163,801), Robbins et al. (U.S. Pat. No. 7,022,472), Mack et al. (U.S. Pat. No. 6,682,890), Tabiti et al. (U.S. Pat. No. 5,888,746), Budiman et al. (US 2009/0098542), Karl (US 2009/0075311), Arjol et al. (US 2008/0286801), Lee et al. (US 2008/0206756), Mori et al. (US 2008/0081333), Wang et al. (US 2008/0058432), Belacel et al. (US 2008/0050723), Stedronsky et al. (US 2008/0020940), An et al. (US 2006/0234254), Eveleigh et al. (US 2004/0146921), and Yeatman et al. (US 2006/0195269). The contents of each of the articles, patents, and patent applications are incorporated by reference herein in their entirety. Exemplary biomarkers that have been associated with colorectal cancers include: 36P6D5; TTK; CDX2; NRG4; TUCAN; hMLH1; hMSH2; M2-PK; CGA7; CJA8; PTP.alpha.; APC; p53; Ki-ras; complement C3a des-arg; alpha1-antitrypsin; transferrin; MMP-11; CA-19-9; TPA; TPS; TIMP-1; C10orf3; carcinoembryonic antigen (CEA); a soluble fragment of cytokeratin 19 (CYFRA 21-1); TAC1; carbohydrate antigen 724 (CA72-4); nicotinamide N-methyltransferase (NNMT); pyrroline-5-carboxylate reductase (PROC); S-adenosylhomocysteine hydrolase (SAHH); IBABP-L polypeptide; and Septin 9.

Biomarkers associated with development of prostate cancer are shown in Sidransky (U.S. Pat. No. 7,524,633), Platica (U.S. Pat. No. 7,510,707), Salceda et al. (U.S. Pat. Nos. 7,432,064 and 7,364,862), Siegler et al. (U.S. Pat. No. 7,361,474), Wang (U.S. Pat. No. 7,348,142), Ali et al. (U.S. Pat. No. 7,326,529), Price et al. (U.S. Pat. No. 7,229,770), O'Brien et al. (U.S. Pat. No. 7,291,462), Golub et al. (U.S. Pat. No. 6,949,342), Ogden et al. (U.S. Pat. No. 6,841,350), An et al. (U.S. Pat. No. 6,171,796), Bergan et al. (US 2009/0124569), Bhowmick (US 2009/0017463), Srivastava et al. (US 2008/0269157), Chinnaiyan et al. (US 2008/0222741), Thaxton et al. (US 2008/0181850), Dahary et al. (US 2008/0014590), Diamandis et al. (US 2006/0269971), Rubin et al. (US 2006/0234259), Einstein et al. (US 2006/0115821), Paris et al. (US 2006/0110759), Condon-Cardo (US 2004/0053247), and Ritchie et al. (US 2009/0127454). The contents of each of the articles, patents, and patent applications are incorporated by reference herein in their entirety. Exemplary biomarkers that have been associated with prostate cancer include: PSA; GSTP1; PAR; CSG; MIF; TADG-15; p53; YKL-40; ZEB; HOXC6; Pax 2; prostate-specific transglutaminase; cytokeratin 15; MEK4; MIP1-β; fractalkine; IL-15; ERG8; EZH2; EPC1; EPC2; NLGN-4Y; kallikrein 11; ABP280 (FLNA); AMACR; AR; BM28; BUB3; CaMKK; CASPASE3; CDK7; DYNAMIN; E2F1; E-CADHERIN; EXPORTIN; EZH2; FAS; GAS7; GS28; ICBP90; ITGA5; JAGGED1; JAM1; KANADAPTIN; KLF6; KRIP1; LAP2; MCAM; MIB1 (MKI67); MTA1; MUC1; MYOSIN-VI; P27; P63; P27; PAXILLIN; PLCLN; PSA(KLK3); RAB27; RBBP; RIN1; SAPKα; TPD52; XIAP; ZAG; and semenogelin II.

Biomarkers associated with development of pancreatic cancer are shown in Sahin et al. (U.S. Pat. No. 7,527,933), Rataino et al. (U.S. Pat. No. 7,507,541), Schleyer et al. (U.S. Pat. No. 7,476,506), Domon et al. (U.S. Pat. No. 7,473,531), McCaffey et al. (U.S. Pat. No. 7,358,231), Price et al. (U.S.

Pat. No. 7,229,770), Chan et al. (US 2005/0095611), Mitchl et al. (US 2006/0258841), and Faca et al. (PLoS Med 5(6):e123, 2008). The contents of each of the articles, patents, and patent applications are incorporated by reference herein in their entirety. Exemplary biomarkers that have been associated with pancreatic cancer include: CA19.9; 36P6D5; NRG4; ASCT2; CCR7; 3C4-Ag; KLK11; Fibrinogen γ; and YKL40.

Biomarkers associated with development of lung cancer are shown in Sahin et al. (U.S. Pat. No. 7,527,933), Hutteman (U.S. Pat. No. 7,473,530), Bae et al. (U.S. Pat. No. 7,368,255), Wang (U.S. Pat. No. 7,348,142), Nacht et al. (U.S. Pat. No. 7,332,590), Gure et al. (U.S. Pat. No. 7,314,721), Patel (U.S. Pat. No. 7,300,765), Price et al. (U.S. Pat. No. 7,229,770), O'Brien et al. (U.S. Pat. Nos. 7,291,462 and 6,316,213), Muramatsu et al. (U.S. Pat. No. 7,090,983), Carson et al. (U.S. Pat. No. 6,576,420), Giordano (U.S. Pat. No. 5,840,506), Guo (US 2009/0062144), Tsao et al. (US 2008/0176236), Nakamura et al. (US 2008/0050378), Raponi et al. (US 2006/0252057), Yip et al. (US 2006/0223127), Pollock et al. (US 2006/0046257), Moon et al. (US 2003/0224509), and Budiman et al. (US 2009/0098543). The contents of each of the articles, patents, and patent applications are incorporated by reference herein in their entirety. Exemplary biomarkers that have been associated with lung cancer include: COX-2; COX4-2; RUNX3; aldoketoreductase family 1, member B 10; peroxiredoxin 1 (PRDX1); TNF receptor superfamily member 18; small proline-rich protein 3 (SPRR3); SOX1; SC6; TADG-15; YKL40; midkine; DAP-kinase; HOXA9; SCCE; STX1A; HIF1A; CCT3; HLA-DPB1; MAFK; RNF5; KIF11; GHSR1b; NTSR1; FOXM1; and PUMP-1.

Biomarkers associated with development of skin cancer (e.g., basal cell carcinoma, squamous cell carcinoma, and melanoma) are shown in Roberts et al. (U.S. Pat. No. 6,316,208), Polsky (U.S. Pat. No. 7,442,507), Price et al. (U.S. Pat. No. 7,229,770), Genetta (U.S. Pat. No. 7,078,180), Carson et al. (U.S. Pat. No. 6,576,420), Moses et al. (US 2008/0286811), Moses et al. (US 2008/0268473), Dooley et al. (US 2003/0232356), Chang et al. (US 2008/0274908), Alani et al. (US 2008/0118462), Wang (US 2007/0154889), and Zetter et al. (US 2008/0064047). The contents of each of the articles, patents, and patent applications are incorporated by reference herein in their entirety. Exemplary biomarkers that have been associated with skin cancer include: p27; Cyr61; ADAMTS-7; Cystatin B; Chaperonin 10; Profilin; BRAF; YKL-40; DDX48; erbB3-binding protein; biliverdin reductase; PLAB; L1CAM; SAA; CRP; SOX9; MMP2; CD10; and ZEB.

Biomarkers associated with development of multiple myeloma are shown in Coignet (U.S. Pat. No. 7,449,303), Shaughnessy et al. (U.S. Pat. No. 7,308,364), Seshi (U.S. Pat. No. 7,049,072), and Shaughnessy et al. (US 2008/0293578, US 2008/0234139, and US 2008/0234138). The contents of each of the articles, patents, and patent applications are incorporated by reference herein in their entirety. Exemplary biomarkers that have been associated with multiple myeloma include: JAG2; CCND1; MAF; MAFB; MMSET; CST6; RAB7L1; MAP4K3; HRASLS2; TRAIL; IG; FGL2; GNG11; MCM2; FLJ10709; TRIM13; NADSYN1; TRIM22; AGRN; CENTD2; SESN1; TM7SF2; NICKAP1; COPG; STAT3; ALOX5; APP; ABCB9; GAA; CEP55; BRCA1; ANLN; PYGL; CCNE2; ASPM; SUV39H2; CDCA7; CDCA2; HFE; RIF1; NEIL3; SLC4A7; FXYD5; MCC; MKNK2; KLHL24; DLC1; OPN3; B3GALNT1; SPRED1; ARHGAP25; RTN2; WNT16; DEPDC1; STT3B; ECHDC2; ENPP4; SAT2; SLAMF7; MAN1C1; INTS7; ZNF600; L3MBTL4; LAPTM4B; OSBPL10; KCNS3; THEX1. CYB5D2; UNC93B1; SIDT1; TMEM57; HIGD24; FKSG44; C14orf28; LOC387763; TncRNA; C18orf1; DCUN1D4; FANCI; ZMAT3; NOTCH1; BTG2; RAB1A; TNFRSF10B; HDLBP; RIT1; KIF2C; S100A4; MEIS1; SGOL2; CD302; COX2; C5orf34; FAM111B; C18orf54; and TP53.

Biomarkers associated with development of leukemia are shown in Ando et al. (U.S. Pat. No. 7,479,371), Coignet (U.S. Pat. Nos. 7,479,370 and 7,449,303), Davi et al. (U.S. Pat. No. 7,416,851), Chiorazzi (U.S. Pat. No. 7,316,906), Seshi (U.S. Pat. No. 7,049,072), Van Baren et al. (U.S. Pat. No. 6,130,052), Taniguchi (U.S. Pat. No. 5,643,729), Insel et al. (US 2009/0131353), and Van Bockstaele et al. (Blood Rev. 23(1):25-47, 2009). The contents of each of the articles, patents, and patent applications are incorporated by reference herein in their entirety. Exemplary biomarkers that have been associated with leukemia include: SCGF; JAG2; LPL; ADAM29; PDE; Cryptochrome-1; CD49d; ZAP-70; PRAME; WT1; CD15; CD33; and CD38.

Biomarkers associated with development of lymphoma are shown in Ando et al. (U.S. Pat. No. 7,479,371), Levy et al. (U.S. Pat. No. 7,332,280), and Arnold (U.S. Pat. No. 5,858,655). The contents of each of the articles, patents, and patent applications are incorporated by reference herein in their entirety. Exemplary biomarkers that have been associated with lymphoma include: SCGF; LMO2; BCL6; FN1; CCND2; SCYA3; BCL2; CD79a; CD7; CD25; CD45RO; CD45RA; and PRAD1 cyclin.

Biomarkers associated with development of bladder cancer are shown in Price et al. (U.S. Pat. No. 7,229,770), Orntoft (U.S. Pat. No. 6,936,417), Haak-Frendscho et al. (U.S. Pat. No. 6,008,003), Feinstein et al. (U.S. Pat. No. 6,998,232), Elting et al. (US 2008/0311604), and Wewer et al. (2009/0029372). The contents of each of the patent applications and each of these patents are incorporated by reference herein in their entirety. Exemplary biomarkers that have been associated with bladder cancer include: NT-3; NGF; GDNF; YKL-40; p53; pRB; p21; p27; cyclin E1; Ki67; Fas; urothelial carcinoma-associated 1; human chorionic gonadotropin beta type II; insulin-like growth factor-binding protein 7; sorting nexin 16; chondroitin sulfate proteoglycan 6; cathepsin D; chromodomain helicase DNA-binding protein 2; nell-like 2; tumor necrosis factor receptor superfamily member 7; cytokeratin 18 (CK18); ADAM8; ADAM10; ADAM12; MMP-2; MMP-9; KAI1; and bladder tumor fibronectin (BTF).

Metabolites

In certain embodiments, the biomarker is a metabolite. A metabolite generally refers to any compound that is an intermediate or product of metabolism or a compound that is necessary for or taking part in a particular metabolic process. A metabolite is not limited to any particular class of compounds, and includes, for example, classes of compounds such as lipids, carbohydrates, amino acids, organic acids, sterols, and nucleosides. A metabolite may be a primary metabolite (i.e., a compound that is directly involved in normal growth, development, and reproduction) or a secondary metabolite (i.e., a compound that is not directly involved in those processes, but usually has an important ecological function). In an exemplary embodiment, a metabolite may be a low molecular weight compounds (<1 kDa) that is the product of a chemical reaction or reactions that occur inside cells of living organisms, such as within human or animal or plant tissue. Living organisms also encompasses microorganisms, such as bacteria and fungus. In certain embodiments, a metabolite is an intermediate or a product of an enzymatic reaction, such as an enzymatic reaction that occurs within the cells of normal tissue or abnormal tissue, such as diseased tissue, such as cancerous tissue. For considerations related to metabolites are described, for example, in Harris et al., (Biochemical Facts behind the Definition and Properties of Metabolites, found at the website for the FDA on the page related to metabolites), the content of which is incorporated by reference herein in its entirety.

Abnormal metabolite levels may be associated with a disease state, for example metabolic diseases, cardiovascular diseases, kidney diseases, liver diseases, gastrointestinal diseases, cancers, etc. In certain embodiments, the metabolites analyzed result from genetic aberrations that constitute particular disease states, including cancer, including endogenous compounds whose constitutive levels vary and de novo compounds (Dill, et al., A European Journal 17, 2897-2902 (2011); Dill et al., Analytical and bioanalytical chemistry 398, 2969-2978 (2010); Eberlin et al. Analytical chemistry 82, 3430-3434 (2010); and Eberlin et al. Proceedings of the National Academy of Sciences (2013)). Metabolites of interest are of diagnostic and/or prognostic value.

Metabolites may include those derived from the pathways associated with energy production, cellular signaling, and structure. Such metabolites include aerobic and anaerobic cellular respiration and synthesis of lipid constituents. The compounds from the alpha-hydroxy acid (AHA) class are implicated. The production of alpha-hydroxyglutaric acid (2-HG) in human brain tumors is particularly included. Mutations in isocitrate dehydrogenases (IDHs) deviates prototypical conversion of isocitrate to alpha-ketogluterate via oxidative decarboxylation. Additionally, beta and gamma hydroxy acids are implicated. Metabolites of interest in neural cancers include small amino acid neurotransmitters (e.g. aspartate, glutamate, GABA, glycine, etc), neuropeptides, opioids (e.g. endorphin), monoamines (e.g. dopamine and serotonin), and diamines (e.g. histamine). These metabolites and related anabolic and catabolic intermediates are included, such as in the case of N-acetylaspartylgluterate (NAAG) synthesized de novo from N-acetylaspartate and glutamic acid. Sulfonic acid metabolites are also implicated, e.g. taurine.

Also included are specific modifications facilitated by enzymatic linkage of sulfate groups and similar functionalities, i.e. cholesterol sulfate. Endogenous compounds representing what might vary in concentration include the major metabolites of the tricarboxylic acid cycle (e.g. citrate, isocitrate, alpha-ketogluterate, succinate, fumarate, malate, and oxaloacetate), glycolysis (e.g. glucose, glucose-6-phosphate, fructose-6-phosphate, glyceraldehyde-3-phosphate, etc), and similar energy production metabolites. Signaling metabolites including but not limited to prostaglandins, cytokines, and hormones would be similarly included. Finally, lipid constituents, known to vary in accordance with disease state, should be noted as important metabolites (Eberlin, et al., Angewandte Chemie 49, 5953-5956 (2010); and Eberlin, et al., Cancer research 72, 645-654 (2012)). In certain embodiments, the metabolites analyzed are aspartic acid, ascorbic acid, glutamic acid, and taurine (inverse dependence).

Porous Materials

Porous materials that may be used as tips for probes of the invention are described, for example in U.S. Pat. No. 8,859,956, the content of which is incorporated by reference herein in its entirety. In certain embodiments, the porous material is any cellulose based material. In other embodiments, the porous material is a non-metallic porous material, such as cotton, linen wool, or synthetic textiles. In still other embodiments, the porous material is paper. In other embodiments, the porous material is a metallic porous material. In certain embodiments, the porous material is a plurality of materials (e.g., a combination of different materials), that be combinations of any of the above.

Ion Traps and Mass Spectrometers

Any ion trap known in the art can be used in systems of the invention. Exemplary ion traps include a hyperbolic ion trap (e.g., U.S. Pat. No. 5,644,131, the content of which is incorporated by reference herein in its entirety), a cylindrical ion trap (e.g., Bonner et al., International Journal of Mass Spectrometry and Ion Physics, 24(3):255-269, 1977, the content of which is incorporated by reference herein in its entirety), a linear ion trap (Hagar, Rapid Communications in Mass Spectrometry, 16(6):512-526, 2002, the content of which is incorporated by reference herein in its entirety), and a rectilinear ion trap (U.S. Pat. No. 6,838,666, the content of which is incorporated by reference herein in its entirety).

Any mass spectrometer (e.g., bench-top mass spectrometer of miniature mass spectrometer) may be used in systems of the invention and in certain embodiments the mass spectrometer is a miniature mass spectrometer. An exemplary miniature mass spectrometer is described, for example in Gao et al. (Anal. Chem. 2008, 80, 7198-7205.), the content of which is incorporated by reference herein in its entirety. In comparison with the pumping system used for lab-scale instruments with thousands of watts of power, miniature mass spectrometers generally have smaller pumping systems, such as a 18 W pumping system with only a 5 L/min (0.3 m$^3$/hr) diaphragm pump and a 11 L/s turbo pump for the system described in Gao et al. Other exemplary miniature mass spectrometers are described for example in Gao et al. (Anal. Chem., 2008, 80, 7198-7205.), Hou et al. (Anal. Chem., 2011, 83, 1857-1861.), and Sokol et al. (Int. J. Mass Spectrom., 2011, 306, 187-195), the content of each of which is incorporated herein by reference in its entirety.

Figure 13:
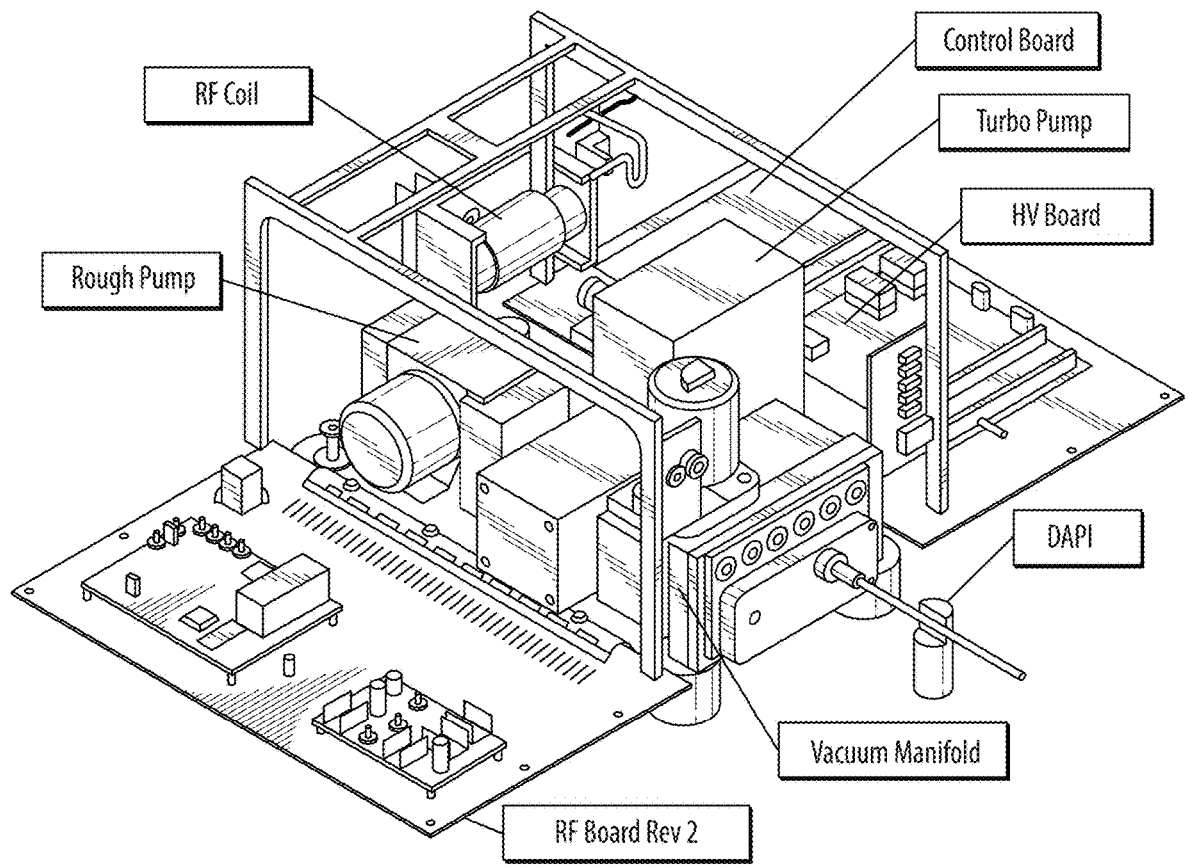
FIG. 13 is a picture illustrating various components and their arrangement in a miniature mass spectrometer.
Figure 14:
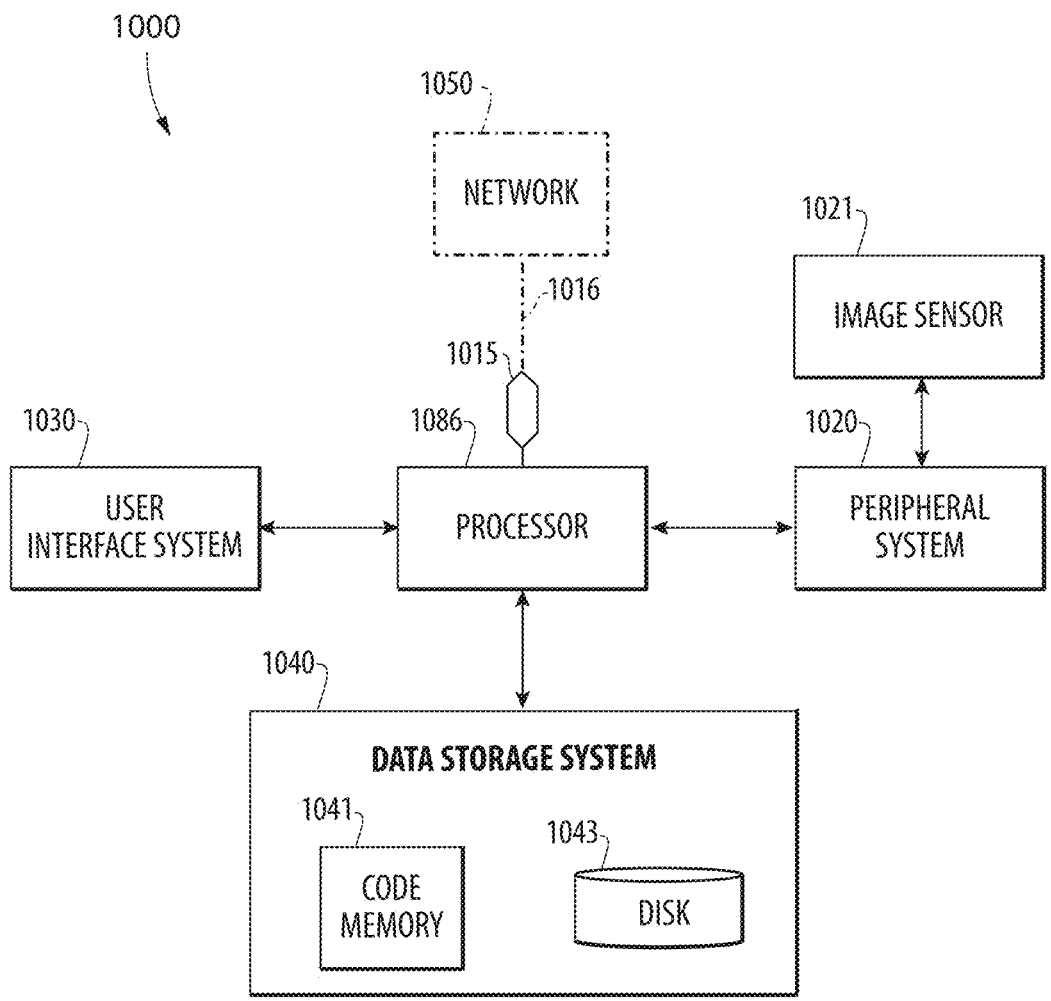
FIG. 14 shows a high-level diagram of the components of an exemplary data-processing system for analyzing data and performing other analyses described herein, and related components.

FIG. 13 is a picture illustrating various components and their arrangement in a miniature mass spectrometer. The control system of the Mini 12 (Linfan Li, Tsung-Chi Chen, Yue Ren, Paul I. Hendricks, R. Graham Cooks and Zheng Ouyang "Miniature Ambient Mass Analysis System" Anal. Chem. 2014, 86 2909-2916, DOI: 10.1021/ac403766c; and 860. Paul I. Hendricks, Jon K. Dalgleish, Jacob T. Shelley, Matthew A. Kirleis, Matthew T. McNicholas, Linfan Li, Tsung-Chi Chen, Chien-Hsun Chen, Jason S. Duncan, Frank Boudreau, Robert J. Noll, John P. Denton, Timothy A. Roach, Zheng Ouyang, and R. Graham Cooks "Autonomous in-situ analysis and real-time chemical detection using a backpack miniature mass spectrometer: concept, instrumentation development, and performance" Anal. Chem., 2014, 86 2900-2908 DOI: 10.1021/ac403765x, the content of each of which is incorporated by reference herein in its entirety), and the vacuum system of the Mini 10 (Liang Gao, Qingyu Song, Garth E. Patterson, R. Graham Cooks and Zheng Ouyang, "Handheld Rectilinear Ion Trap Mass Spectrometer", Anal. Chem., 78 (2006) 5994-6002 DOI: 10.1021/ac061144k, the content of which is incorporated by reference herein in its entirety) may be combined to produce the miniature mass spectrometer shown in FIG. 7. It may have a size similar to that of a shoebox (H20×W25 cm×D35 cm). In certain embodiments, the miniature mass spectrometer uses a dual LIT configuration, which is described for example in Owen et al. (U.S. patent application Ser. No. 14/345,672), and Ouyang et al. (U.S. patent application Ser.

No. 61/865,377), the content of each of which is incorporated by reference herein in its entirety.

System Architecture

FIG. 8 is a high-level diagram showing the components of an exemplary data-processing system 1000 for analyzing data and performing other analyses described herein, and related components. The system includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The data described above may be obtained using detector 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 which in one embodiment may be capable of real-time calculations (and in an alternative embodiment configured to perform calculations on a non-real-time basis and store the results of calculations for use later) can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (e.g., a tablet) connected, e.g., via a network or a null-modem cable, or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), Universal Serial Bus (USB) interface memory device, erasable programmable read-only memories (EPROM, EEPROM, or Flash), remotely accessible hard drives, and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects. These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors) to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

Discontinuous Atmospheric Pressure Interface (DAPI)

In certain embodiments, the systems of the invention can be operated with a Discontinuous Atmospheric Pressure Interface (DAPI). A DAPI is particularly useful when coupled to a miniature mass spectrometer, but can also be used with a standard bench-top mass spectrometer. Discontinuous atmospheric interfaces are described in Ouyang et al. (U.S. Pat. No. 8,304,718 and PCT application number PCT/US2008/065245), the content of each of which is incorporated by reference herein in its entirety.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Swab spray mass spectrometry is an ambient ionization technique (ionization of unprocessed sample in the open air) that uses medical swabs (swab spray MS). This technique has potential intraoperative applications in quickly identifying the disease state of cancerous tissue and in better characterizing the resection margin. To explore this potential we studied 29 human brain tumor specimens by swab spray MS and obtained evidence that swab spray MS can provide diagnostic molecular information that is relevant to brain cancer. Swab spray MS involves the physical sampling of tissue using a medical swab on a spatial scale of a few $mm^2$ with subsequent ionization occurring directly from the swab tip upon addition of solvent (25 uL/min) and application of a high voltage (−6.5 kV). Using a tertiary mixture of acetonitrile, N,N-dimethylformamlde and ethanol, membrane-derived phospholipids and oncometabolites are extracted from the tissue, incorporated into the sprayed microdroplets and so vacuumed into the mass spectrometer, and visualized in the resulting mass spectra. The tumor cell load was assessed from the complex phospholipid MS profile and separately by measurement of N-acetyl-aspartic acid (NAA). Mutation status of the isocitrate dehydrogenase gene (IDH) was determined via detection of the oncometabolite 2-hydroxyglutaric acid (2HG). The lack of sample pretreatment makes swab spray MS a feasible intraoperative strategy for rapid surgical assessment.

Example 1: Materials and Methods

Cryopreserved human neurological specimens were obtained from 29 patients by the Biorepository of the Indianapolis Methodist Research Institute (Purdue IRB #1410015344). The list of the samples analyzed in this study is reported in Table 1. For each sample, a few tissue sections (15-um thickness) were cut using a cryotome in order to obtain a flat surface of the tissue. The last section cut was H&E stained for blind pathological examination. The H&E staining protocol is described elsewhere (18). The sample was then allowed to thaw at room temperate; the flat surface of the tissue, adjacent to the section that was stained, was touched with the swab to perform the TS-MS experiments. Regions of interest in the tissue sections were codified based on pathological evaluation as glioma (G) or infiltrated tissue (IT)—specifying whether grey matter (GM), white matter (WM), a mixture of both, or tissue not otherwise specified (nos). Estimation of tumor cell percentage (TCP) was provided by the pathologist in the categories of low (<33%), medium (34-67%), and high (>67%). For all the specimens, another portion of the tissue had been previously used for preparation of tissue sections and smears and analyzed by DESI-MS imaging. Results are reported elsewhere (18, 19). Homogenized mouse brain (Purdue IRB #1704001561) was used for method development. Tissue specimens were stored at −80° C. prior to analysis.

Experiments were performed using sterile medical swabs, model 160C, provided by Copan Diagnostics (Murrieta, Calif.). The swabs have an aluminum handle and rayon mini-tip of fused shape and largest diameter of ~2.4 mm (FIG. 12). The swabs are packaged in individual tubes for easy transport and storage. They are mounted in a plastic cap that serves as a convenient holder. Each tube and cap assembly is sealed with a tamper proof label for assurance of sterility and chain of custody. These swabs are commercialized for purposes other than ESI probes for MS analysis. Swab spray experiments were performed by touching gently a region of interest of a sample and rotating the swab on its shaft to transfer tissue on the swab tip. Each swab was weighted before and after the touch to measure tissue quantity transferred to the swab tip, and then submitted to MS analysis with no further treatment. Multiple regions of interest were swabbed for most samples showing macroscopically-heterogeneous areas (Table 1).

Electrospray was generated using a mixture of acetonitrile-dimethylformamide-ethanol (ACN-DMF-EtOH) in a ratio of 45:5:50% v/v, doped with 250 ng/mL of octyl B-D-glucopyranoside (non-ionic surfactant, >98% pure) and 10 g/mL uof the internal standard NAA-d3. All solvents and standards were purchased from Sigma Aldrich (Minneapolis, Minn.).

Mass Spectrometry

All experiments were performed using a linear ion trap mass spectrometer (LTQ, Thermo Scientific, San Jose, Calif.). High voltage was applied to the swab shaft using a custom high voltage cable, the instrument high voltage supply, and a copper clip. Solvent was applied continuously on the swab tip via a fused silica capillary and external syringe pump. A customized interface that locks directly to the mass spectrometer was built to affix the swab in front of the instrument (FIG. 6 panels A-B). The swab was oriented vertically with the tip directly above the MS inlet capillary, which was bent 90° upwards. The swab was positioned 5-8 mm above the inlet. A precision motion control system was used to adjust the position of the swab whenever necessary. The syringe pump flow rate was set at 50 uL/min for about 30 s, accounting for dead volume and wetting the swab tip. When the swab tip was visibly wet, high voltage (−6.5 kV) was applied to the metallic handle. Solvent flow rate was changed to 25 uL/min. Full scan mass spectra over m/z 700-1000 were acquired in negative ion mode first, then a second acquisition over the mass range m/z 80-200 was performed, then collision induced dissociation $MS^2$ product ion scans of NAA (precursor ion m/z 174) and NAA-$d_3$ (precursor ion m/z 177) were acquired, followed by $MS^3$ product ion scans of 2HG (m/z 147→129). Total acquisition time was 1.2 min; approx. 15 seconds were acquired for each mode so that spray and signal stability could be evaluated. $MS^n$ data other than for NAA and 2HG identification were acquired separately when additional structural information was needed for compound identification. The automatic gain control was always activated to adjust for variable ion flux. Additional details on the MS instrumental settings are reported in Table 2.

TABLE 2

Table S2. Instrumental Settings

| Full Scan MS | Lipid Profile | Metabolite Profile |
|---|---|---|
| Mass range | m/z 700-1000 | m/z 80-200 |
| Tuned mass | m/z 786 | m/z 174 |
| Tube lenses potential | −80 V | −20 V |
| Capillary voltage | 0 V | −8 V |
| Microscans | 2 | |
| Injection time | 25 ms | |
| Capillary temperature | 275° C. | |
| Capillary voltage | −6.5 kV | |

| $MS^n$ CID* fragmentation | NAA | NAA-$d_3$ | 2-HG |
|---|---|---|---|
| $MS^n$ transitions | m/z 174 → o | m/z 177 → o | m/z 147 → 129 → o |
| Tube lenses potential | −20 V | | |
| Capillary voltage | −8 V | | |
| Microscans | 2 | | |
| Injection time | 25 ms | | |
| Collision Energy (a.u.) | 28 | | |
| Q value | 0.3 | | |

Signal-to-noise ratios were calculated using ion intensities at peaks' height and signal intensities at the onset of the peaks. Box-plots have been computed using normalized signal intensities of NAA and 2HG. Ion counts were normalized to the internal standard (NAA-$d_3$) and to the weight of the tissue (g) transferred on the swab tip.

For each swab tested, videos of the spray plume were recorded to observe the electrospray behavior. A Watec WAT-704R camera was used to acquire the videos; the software Cyberlink PowerDirector v.14 was used to record them; Adobe Premier Pro CC was used for video editing when necessary. The spray plume was illuminated with a red laser pointer as shown in FIG. 6 panels A-B.

Example 2: Electrospray Generation Using Swab Spray

The swabs are unconventional probes for electrospray because of their fused shape and large tip (>1 mm). Swab spray differs from regular electrospray in that the solvent is pumped on a rough and porous surface, it is initially absorbed and then becomes suspended in a droplet at the apex of the swab tip once the porous material is completely saturated. When high voltage is applied to the handle of the swab, the voltage is transferred to the solvent at the swab tip. The suspended droplet becomes elongated. The elongation reduces droplet diameter, which in turn increases the electric field strength such that it exceeds the solvent surface tension resulting in the electrospray generation. FIG. 6 panel B shows the electrospray plume. The figure shows the electrospray plume formation as described above and its remarkable stability over time. The solvent system used for electrospray generation was a mixture of ACN, DMF, and EtOH. The large fraction of EtOH (50%) and the non-ionic surfactant served primarily the purpose of decreasing the surface tension of the solution such that a stable electrospray was created before any electrical discharge occurred. It was empirically determined that a swab-to-inlet distance of 5-8 mm resulted in consistent spray, balancing the electric field strength with the electrospray plume. The flow rate of the solvent had to be slightly adjusted (25±3 μL/min, on average) for each swab analyzed to correct for differences in shape and tip dimension. It was possible to generate an electrospray from all the swabs analyzed.

What is claimed is:

1. A method for analyzing a sample, the method comprising:
    contacting a distal portion of a probe to a sample such that a portion of the sample is retained on the distal portion of the probe;
    positioning the distal portion of the probe directly vertically above a distal end of an upward opening inlet of a mass spectrometer;
    applying solvent and voltage to the probe to generate ions of the sample that are downwardly expelled from the probe and into the inlet of the mass spectrometer; and
    analyzing the ions in the mass spectrometer, thereby analyzing the sample.

2. The method according to claim 1, wherein the sample is an in vivo human tissue sample and a portion of the in vivo human tissue sample is retained on the distal portion of the probe.

3. The method according to claim 2, wherein the in vivo human tissue sample is along a surface of a resection cavity of the human.

4. The method according to claim 3, further comprising determining if the in vivo human tissue sample comprises abnormal tissue.

5. The method according to claim 4, wherein the abnormal tissue is diseased tissue.

6. The method according to claim 5, wherein the diseased tissue is cancerous tissue.

7. The method according to claim 6, wherein the cancerous tissue is from a tumor.

8. A method for assessing a tissue, the method comprising:

contacting a medical swab to a tissue in a manner that a portion of the tissue is retained on the medical swab;

generating ions of one or more analytes from the portion of the tissue retained on the medical swab by:

positioning the portion of the tissue directly vertically above a distal end of an upward opening inlet of a mass spectrometer; and applying solvent and voltage to the portion of the tissue to generate ions thereof that are downwardly expelled from the swab and into the upward opening inlet; and analyzing the ions in the mass spectrometer, thereby assessing the tissue.

9. The method according to claim 8, wherein the tissue is in vivo tissue.

10. The method according to claim 9, wherein the in vivo tissue is tissue at a resection site in a patient.

11. The method according to claim 10, wherein the analyzing allows for assessment of tumor infiltration into the resection site.

\* \* \* \* \*